(12) United States Patent
Song

(10) Patent No.: US 10,660,933 B2
(45) Date of Patent: May 26, 2020

(54) COMPOSITIONS AND METHODS FOR INHIBITION OF BACTERIAL INFECTIONS IN HUMAN ENDOCERVIX

(71) Applicant: University of Maryland, College Park, College Park, MD (US)

(72) Inventor: Wenxia Song, Olney, MD (US)

(73) Assignee: University of Maryland, College Park, College Park, MD (US)

( * ) Notice: Subject to any disclaimer, the term of this patent is extended or adjusted under 35 U.S.C. 154(b) by 0 days.

(21) Appl. No.: 15/749,548

(22) PCT Filed: Oct. 31, 2016

(86) PCT No.: PCT/US2016/059685
§ 371 (c)(1),
(2) Date: Feb. 1, 2018

(87) PCT Pub. No.: WO2017/075573
PCT Pub. Date: May 4, 2017

(65) Prior Publication Data
US 2018/0207226 A1   Jul. 26, 2018

Related U.S. Application Data

(60) Provisional application No. 62/248,204, filed on Oct. 29, 2015.

(51) Int. Cl.
| | | |
|---|---|---|
| *A61K 38/00* | (2006.01) | |
| *A61K 38/08* | (2019.01) | |
| *A61K 9/00* | (2006.01) | |
| *A61K 31/551* | (2006.01) | |
| *C07K 5/103* | (2006.01) | |
| *C07K 5/09* | (2006.01) | |
| *C07K 5/062* | (2006.01) | |
| *C07K 5/11* | (2006.01) | |
| *C12N 9/12* | (2006.01) | |
| *A61P 31/04* | (2006.01) | |

(52) U.S. Cl.
CPC ............ *A61K 38/08* (2013.01); *A61K 9/0034* (2013.01); *A61K 31/551* (2013.01); *A61P 31/04* (2018.01); *C07K 5/06052* (2013.01); *C07K 5/0817* (2013.01); *C07K 5/1008* (2013.01); *C07K 5/1019* (2013.01); *C12N 9/1205* (2013.01); *A61K 38/00* (2013.01); *A61K 2300/00* (2013.01)

(58) Field of Classification Search
None
See application file for complete search history.

(56) References Cited

U.S. PATENT DOCUMENTS

| | | |
|---|---|---|
| 7,585,844 B2 | 9/2009 | Turner et al. |
| 2004/0192642 A1 | 9/2004 | Yang et al. |
| 2014/0206677 A1* | 7/2014 | Basarab ............... C07D 498/22 514/229.5 |

* cited by examiner

*Primary Examiner* — Jeanette M Lieb
(74) *Attorney, Agent, or Firm* — Hodgson Russ LLP

(57) ABSTRACT

Provided are compositions, methods and devices for prophylaxis and/or therapy of sexually transmitted bacterial infections that infect the female reproductive tract. The compositions methods and devices are used for intravaginal administration of compositions that contain a peptide agent known as PIK and/or a compound known as ML-7. Demonstrations of embodiments are provided for infection models that involve *Neisseria gonorrhoeae*.

11 Claims, 21 Drawing Sheets
Specification includes a Sequence Listing.

SEQUENCE LISTING

```
<160> NUMBER OF SEQ ID NOS: 2

<210> SEQ ID NO 1
<211> LENGTH: 9
<212> TYPE: PRT
<213> ORGANISM: artificial sequence
<220> FEATURE:
<223> OTHER INFORMATION: synthetic peptide which can contain at least
      one D-amino acid

<400> SEQUENCE: 1

Lys Arg Arg Tyr Lys Tyr Lys Lys Arg
1               5

<210> SEQ ID NO 2
<211> LENGTH: 9
<212> TYPE: PRT
<213> ORGANISM: artificial sequence
<220> FEATURE:
<223> OTHER INFORMATION: synthetic peptide that can include at least one
      D-amino acid

<400> SEQUENCE: 2

Arg Lys Lys Tyr Lys Tyr Arg Arg Lys
1               5
```

COMPOSITIONS AND METHODS FOR INHIBITION OF BACTERIAL INFECTIONS IN HUMAN ENDOCERVIX

CROSS REFERENCE TO RELATED APPLICATIONS

This application claims priority to U.S. Provisional Application No. 62/248,204, filed on Oct. 29, 2015, the disclosure of which is hereby incorporated by reference.

STATEMENT REGARDING FEDERALLY SPONSORED RESEARCH

This invention was made with government support under contract no. R21AI103797 awarded by the National Institutes of Health. The government has certain rights in the invention.

FIELD OF THE DISCLOSURE

The disclosure generally relates to infectious disease prevention. More particularly the disclosure generally relates to prophylaxis of sexually transmitted diseases.

BACKGROUND OF THE DISCLOSURE

Colonization and disruption of the epithelium is a major infection mechanism of mucosal pathogens. The epithelium counteracts infection by exfoliating damaged cells while maintaining the mucosal barrier function. The sexually transmitted bacterium *Neisseria gonorrhoeae* (Ng, also referred to in the art as GC) infect the female reproductive tract primarily from the endocervix, causing gonorrhea. However, the mechanism by which Ng overcomes the mucosal barrier remains elusive.

Ng, a Gram-negative bacterium, infects exclusively the mucosal surface of human genital tissues in men and women and causes gonorrhea, one of the most common sexually transmitted infections. In the female reproductive tract (FRT), the epithelium lining of endocervix has been suggested as a primary site for Ng to initiate infection that leads to pelvic inflammatory and disseminated diseases. Ng establishes infection by interacting with various receptors on epithelial cells, such as the binding of opacity-associate protein (Opa) to carcinoembryonic antigen-related cell adhesion molecules (CEACAMs) or heparin sulfate proteoglycans (HSPG). These interactions alter signaling cascades in epithelial cells, such as phosphatidylinositol 3-kinase, phospholipase C, and $Ca^{2+}$ flux. The signaling leads to actin reorganization, which drives microvillus elongation and the subsequent engulfment of Ng. However, how Ng manipulate columnar endocervical epithelial cells through their surface molecules for infection is unknown. A major obstacle against addressing this question has been a lack of infection models better mimicking aspects of human infection, which has in turn hampered the development of effective treatments and preventatives that can inhibit the establishment of Ng infection. Furthermore, The US Center for Disease Control and the World Health Organization have listed gonorrhea as an urgent public and women health issue. Gonorrhea is the second most common bacterial infection, affecting >800,000 people/year in the US and ~80 million people worldwide. Gonorrhea can cause permanent disability and even death, and also increase the risk of HIV and other sexually transmitted diseases (STDs), which is estimated to cost the U.S. health care system ~$17 billion/year. The most vulnerable population are women as STDs are considered a social taboo and most female gonorrhea are asymptomatic, which lead to treatment delay, further transmission, co-infection of other STDs, and severe complications, including chronic pelvic inflammation, life-threatening ectopic pregnancy, infertility, and disseminated infections. In addition to the lack of vaccines, there is also the issue of Ng developing resistance to antibiotics. US surveillance data suggest that it is only a matter of time before Ng becomes resistance to the only remaining effective antibiotics, cephalosporin. Thus, there is an urgent need for alternative preventives for gonorrhea not based on traditional antibiotics, and the development of such preventatives requires an improved research model for Ng infection. The present disclosure is pertinent to these needs.

SUMMARY OF THE DISCLOSURE

The present disclosure provides certain aspects of compositions, methods and devices for prophylaxis and/or therapy of sexually transmitted bacterial infections in the female reproductive tract. The compositions, methods and devices are used for intravaginal administration of compositions that contain a peptide agent comprising the amino acid sequence lys-arg-arg-tyr-lys-tyr-lys-lys-arg (SEQ ID NO:1), and/or a chemical agent known as ML-7 (PubChem CID 4216; commercially available from, for example, EMD MILLIPORE under reference CAS 110448-33-4—Calbiochem; structure:

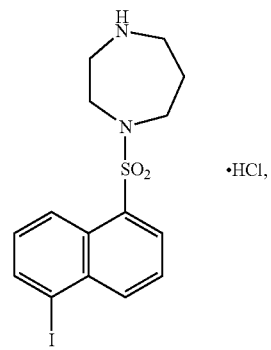 [SMILES: O=S(=O)(c1cccc2c(I)cccc12)N1CCCNCC1 ; "·HCl,"]

or a combination of ML-7 and any of the peptides described herein. Demonstrations of embodiments are provided for human tissue infection models that involve Ng. In particular, embodiments are demonstrated using a new human tissue model, and show that Ng can penetrate into the human endocervix by inducing the exfoliation of columnar epithelial cells. Data are provided which demonstrate that Ng colonization causes endocervical epithelial cells to shed. The shedding results from the disassembly of the apical junctions that seal the epithelial barrier. The apical junction disruption and epithelial exfoliation increase Ng penetration into the endocervical epithelium without reducing bacterial adherence to and invasion into the epithelial cells. Both the epithelial exfoliation and junction disruption require the activation and accumulation of non-muscle myosin II (NMII) at the apical surface and Ng adherent sites. Ng inoculation activates NMII by elevating the levels of the cytoplasmic $Ca^{2+}$ and NMII regulatory light chain phosphorylation. However, the expression of Ng opacity-associated protein inhibits Ng-induced NMII activation and reorganization but does not reduce the cytoplasmic $Ca^{2+}$ level. The inhibitory effects of Opa lead to reductions in junction disruption, epithelial exfoliation, and Ng penetration. Based in part on these discoveries the disclosure demonstrates that Ng modulate infection in the human endocervix by manipulating the activity of NMII and epithelial exfoliation. In this context the disclosure demonstrates that PIK and ML-7 can prohibit Ng from damaging the epithelial barrier and penetrating into human cervical tissues, and that PIK also suppresses Ng growth. The concept of using PIK and ML-7 for prophylaxis and/or therapy of Ng infection is supported using both 3D human epithelial cell and cervical tissue explant models. Accordingly, it is expected that PIK and ML-7 will function as an effective agent for use as an intravaginally applied Ng preventative agent.

DETAILED DESCRIPTION OF THE DISCLOSURE

Figure 1:
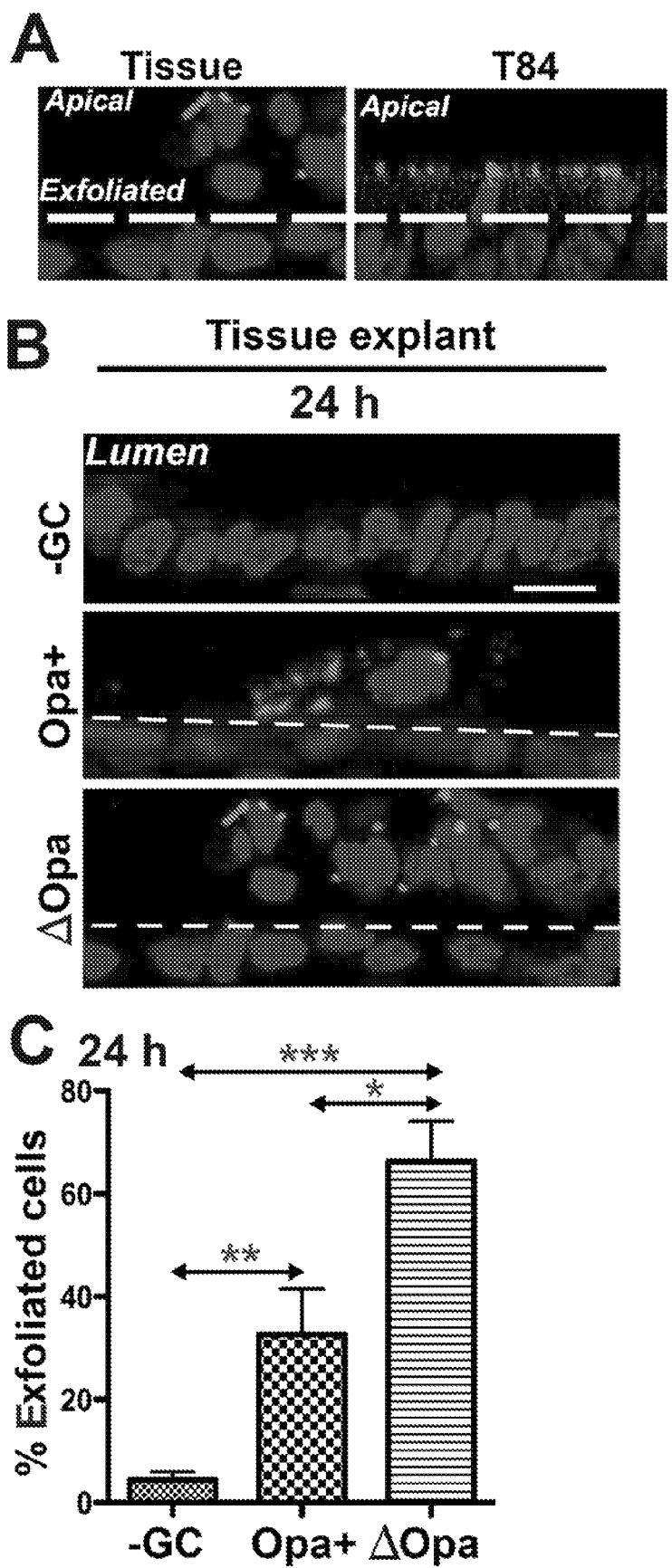
FIG. 1 shows Ng induce exfoliation of polarized epithelial cells from human endocervical tissue explants and T84 monolayers while Opa expression suppresses the exfoliation. Human endocervical tissue pieces (A-C) and polarized T84 monolayers (A, D, and E) were apically incubated with MS11Opa+ or ΔOpa at a MOI of ~10 for 6 or 24 h at 37° C., with unassociated Ng washed off at 6 and 12 h. Cells were fixed, stained for DNA and Ng, and analyzed using 3D-CFM. Shown are representative images that intercept both the apical and basolateral surfaces (Scale bar, 10 µm) (A, B, and D). Based on cell nuclear staining, the average percentage (±SD) of exfoliated epithelial cells was determined by counting the number of Ng-positive epithelial cells localizing above the endocervical epithelium (A-C) and T84 monolayers (A, D, and E), indicated by white dash lines, versus the total number of Ng-associated cells. Shown are the results from >15 randomly selected fields (>50 cells) from three independent experiments or cervixes of two to three human subjects. *$p \leq 0.001$; $p \leq 0.01$; *$p \leq 0.05$.
Figure 1:
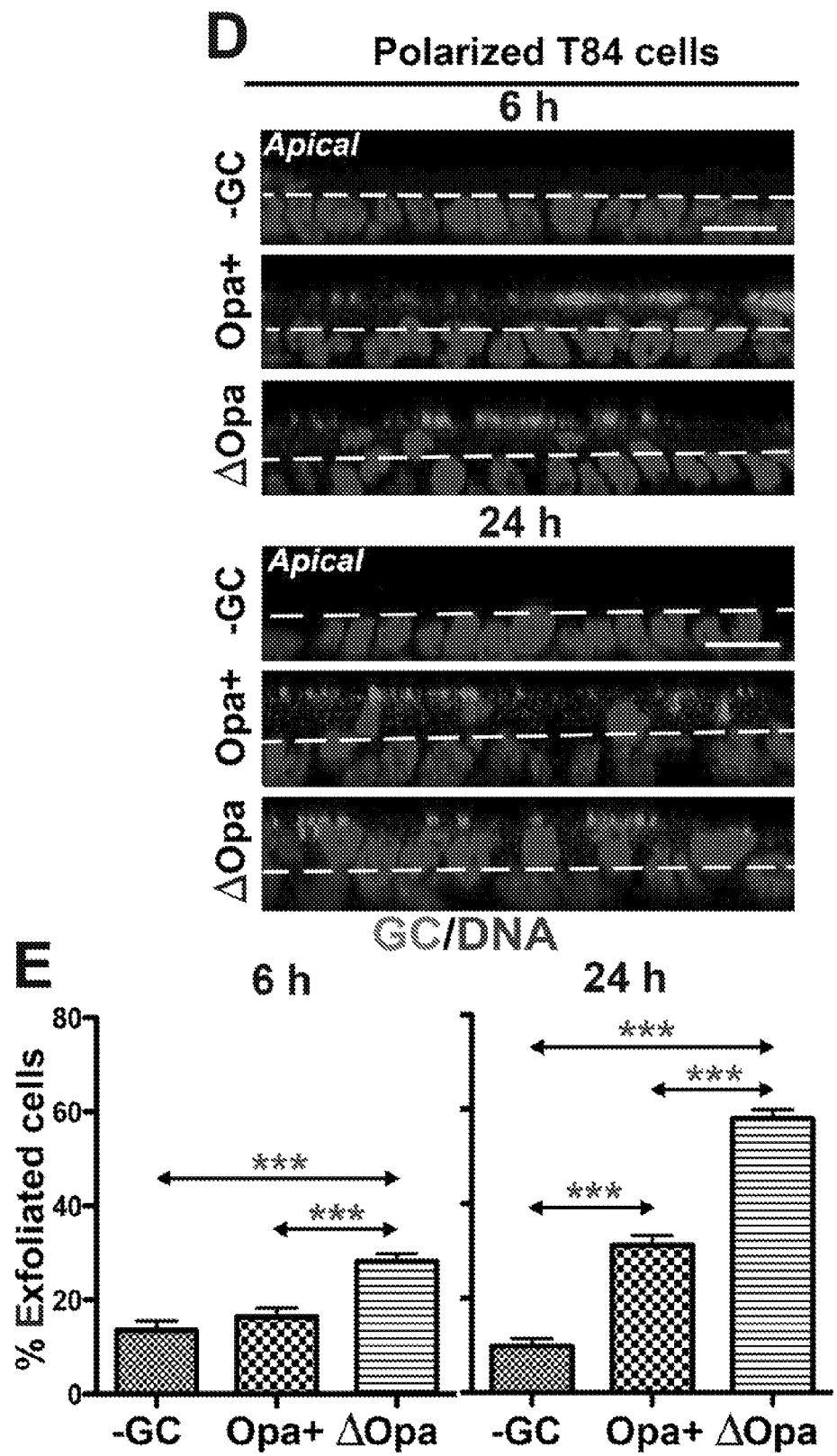

Unless defined otherwise herein, all technical and scientific terms used in this disclosure have the same meaning as commonly understood by one of ordinary skill in the art to which this disclosure pertains.

Every numerical range given throughout this specification includes its upper and lower values, as well as every narrower numerical range that falls within it, as if such narrower numerical ranges were all expressly written herein.

The present disclosure provides compositions and methods for use in prophylaxis of sexually transmitted diseases (STDs). In one aspect the disclosure relates to prophylaxis of NG infection using intravaginal delivery of compositions comprising an inhibitor of myosin light-chain kinase (MLCK). Such compositions may also comprise ML-7. In embodiments the inhibitor of MLCK is a peptide that comprises or consists of the amino acid sequence lys-arg-arg-tyr-lys-tyr-lys-lys-arg (SEQ ID NO:1), or arg-lys-lys-tyr-lys-tyr-arg-arg-lys (SEQ ID NO:2), either of which may be modified such that at least one of the amino acids may be a D amino acid and/or such that the peptide contains one or more non-hydrolyzable bonds, provided that such modified peptides retain at least the same biological activity relative to the same inhibitor having all L-amino acids and hydrolyzable bonds. Any peptide used in this disclosure may be present in an amino acid sequence comprising from 9 to 120 amino acids. Such peptides are described in U.S. Pat. No. 7,585,844. The descriptions in U.S. Pat. No. 7,585,844 of peptides comprising the sequence of SEQ ID NO:1 and SEQ ID NO:2 of this disclosure, derivatives thereof comprising substituted amino acids and D amino acids, amino acid sequences comprising 9 to 120 amino acids, and methods of making such peptides and derivatives, are incorporated herein by reference. In embodiments a peptide used in approaches of this disclosure comprises 9, 8, 7, 6, 5, 4, 3, 2 or 1 D-amino acid(s). An amino acid sequence comprising the sequence of SEQ ID NO:1 of this disclosure, and at least one of its amino acids as D-amino acids is referred to herein as "PIK" and is described in U.S. Pat. No. 7,585,844 as "D-PIK (reverse)". Accordingly the disclosure comprises use of an amino acid sequence comprising from 9 to 120 amino acids, wherein the amino acid sequence comprises SEQ ID NO:1 of this disclosure, wherein at least one of the amino acids in the 9-120 amino acids is in the D-form.

U.S. Pat. No. 7,585,844 describes using PIK and other related peptides for treating intestinal bacterial infections. Similarly, Zolotarevsky, et al. describes PIK in the context of intestinal disease (Zolotarevsky, et al, *A membrane-permeant peptide that inhibits MLC kinase restores barrier function in in vitro models of intestinal disease.* 2002. Gastroenterology 123: 163-172). However, intravaginal use of compositions comprising PIK is distinct from previous disclosures that describe use of PIK in an intestinal environment. This is because there are a significant number of fundamental differences between epithelial cells in the intestine and epithelial cells in the female reproductive tract. These differences relate to differentiation, morphology, physiological functions, and regulation, among other factors.

In more detail, epithelial cells covering the intestine and the reproductive tract are very different. While the intestinal epithelial cells are relatively homogenous, single layered columnar epithelial cells with dense microvilli, epithelial cells in the female reproductive tract, even only the cervix that is the primary location for microbial infection, vary from multilayered squamous, multilayered transformational, and single layered columnar, as well as ciliated and nonciliated. Therefore, the barrier function of these epithelial cells is mediated and regulated by different mechanisms. (Blaskewicz C D, P et al., Biol Reprod. 2011. 85(1):97-104; Corbeil L B, et al., Tissue Cell. 1985. 17(1):53-68). Further, the functions and properties of the epithelial cells in the female reproductive tract, but not the intestine epithelial cells, are regulated heavily by sex hormones, including estrogen, progesterone, and lutropin. (Patton D L, et al. Am J Obstet Gynecol. 2000. 183(4):967-73; Wira C R, et al. Am J Reprod. Immunol. 2010. 63(6):544-65; Wira C R, et al., Nat Rev Immunol. 2015. 15(4):217-30). Further still, epithelial cells in the female reproductive tract express and secrete different proteins. For example, cervical epithelial cells secrete a greater amount of mucus than the intestinal epithelial cells, and the mucus secreted by the cervical epithelial cells has different biochemical composition from those by the intestine epithelial cells and are uniquely regulated by sex hormones. (Zegels G, Va et al., Proteome Sci. 2009. 7:17; Eschenbach D A, et al, Clin Infect Dis. 2000. 30(6):901-7; Chappell C A, et al., Am J Obstet Gynecol. 2014. 211(3):226.e1-7. Epithelial cells in the female reproductive tract also have unique immune sensor functions. (Fung K Y, et al., Science 2013. 339(6123):1088-92;
Wira C R, et al., Am J Reprod Immunol. 2010. 63(6):544-65). Structurally, immune cells in the female reproductive tract are not organized into lymphoid tissues like Peyer patches in the intestine. The immune cells distribute and function differently at different anatomic locations of the reproductive tract, and their immune functions are severely suppressed to accommodate the semen and fetus. (Iijima N, et al., Mucosal Immunol. 2008. 1(6):451-9; Marks E, et al., PLoS Pathog. 2010. 6(11):e1001179; Lesmeister M J, et al., Reprod Biol Endocrinol. 2005. 29; 3: 74); Wira C R, et al., Nat Rev Immunol. 2015. 15(4):217-30. Notably, different microbiomes colonize the mucosal surface of the intestine and the female reproductive tract. (Brotman R M, et al., J Clin Invest. 2011. 121(12):4610-7; Lamont RF1, et al., BJOG. 2011. 118(5):533-49; Nunn K L, et al., Yale J Biol Med. 2016. 89(3):331-337), and what is more, different microbial pathogens infect the human intestine and the human cervix. The human intestinal microbial pathogens, including enteropathogenic *E. Coli* (EPEC), enterohemorrhagic *E. coli* (EHEC), *Vibrio cholerae, Yersinia, Clostridium difficile*, and *Shigella flexineri*, do not infect the mucosal surface of the female reproductive tract. The sexually transmitted microbial pathogens, *Neisseria gonorrhoeae, Treponema pallidum* (syphilis), and *Chlamydia trachomatis* primarily infect from the mucosal surface of the genital tract, but not the intestine. Thus, the skilled artisan will recognize that the approach of the present disclosure is distinct from previous uses of PIK.

In general the present disclosure comprises intravaginal administration of a composition comprising PIK for prophylaxis and/or therapy, and compositions and kits useful for such administration. In certain approaches the present disclosure provides for prophylaxis of a bacterial infection. "Prophylaxis" as used herein means complete or partial prevention of a bacterial infection or disease caused by the infection, or complete or partial prevention of the development of symptoms of that infection or disease, or a delay in the onset of an infection or disease caused by the infection, or its symptoms. In embodiments, a prophylactic effect comprises inhibiting Ng from damaging the vaginal and/or cervical epithelial barrier and/or Ng penetrating into cervical tissue. "Effective amount" means an amount of PIK sufficient to result in the desired response. In certain embodiments methods of the invention are also suitable for achieving a therapeutic response, meaning a reduction of Ng growth in an individual who has an existing Ng infection. In embodiments compositions comprising PIK include PIK in from 1 µM to 250 µM concentrations. In non-limiting embodiments PIK is used in an effective amount as a concentration on the human endocervical tissue of about 100 uM to 250 uM. Volumes will be dictated by the area of the cervical surface. In embodiments, and based in part on volume of vaginal antifungal cream, the volume of a 100 uM to 250 uM composition comprising PIK will be from 1-50 ml. In embodiments, the composition comprises approximately 1.6 oz, or 47 ml. In certain and non-limiting examples, practicing a method of this disclosure results in a reduction of Ng-associated urethritis, vulvovaginitis, and/or a reduction of purulent discharge, and/or dysuria. In embodiments, the disclosure results in inhibition of endocervical infection. In embodiments, the disclosure results in inhibiting Ng adherence, such as inhibiting attachment to microvilli of nonciliated columnar epithelial cells, and/or penetrance of epithelial cells. In embodiments, the disclosure results in an inhibition of parasite-directed endocytosis. In embodiments, the disclosure results in a reduction in bacteremia and/or disseminated bacterial infection. In embodiments the disclosure results in a reduction in asymptomatic infections of the vagina, urethra and/or cervix. In embodiments the disclosure pertains to administering compositions described herein to an individual in need thereof. Such an individual may be, for example, at risk for contracting an STD, including but not necessarily limited to Ng. In embodiments it is considered that practicing the invention can result in a lowering and/or prophylaxis of infections caused by pathogenic agents that are known to cause co-infection with Ng, such as *Chlamydia*, syphilis, and human immunodeficiency virus (HIV).

Figure 3:
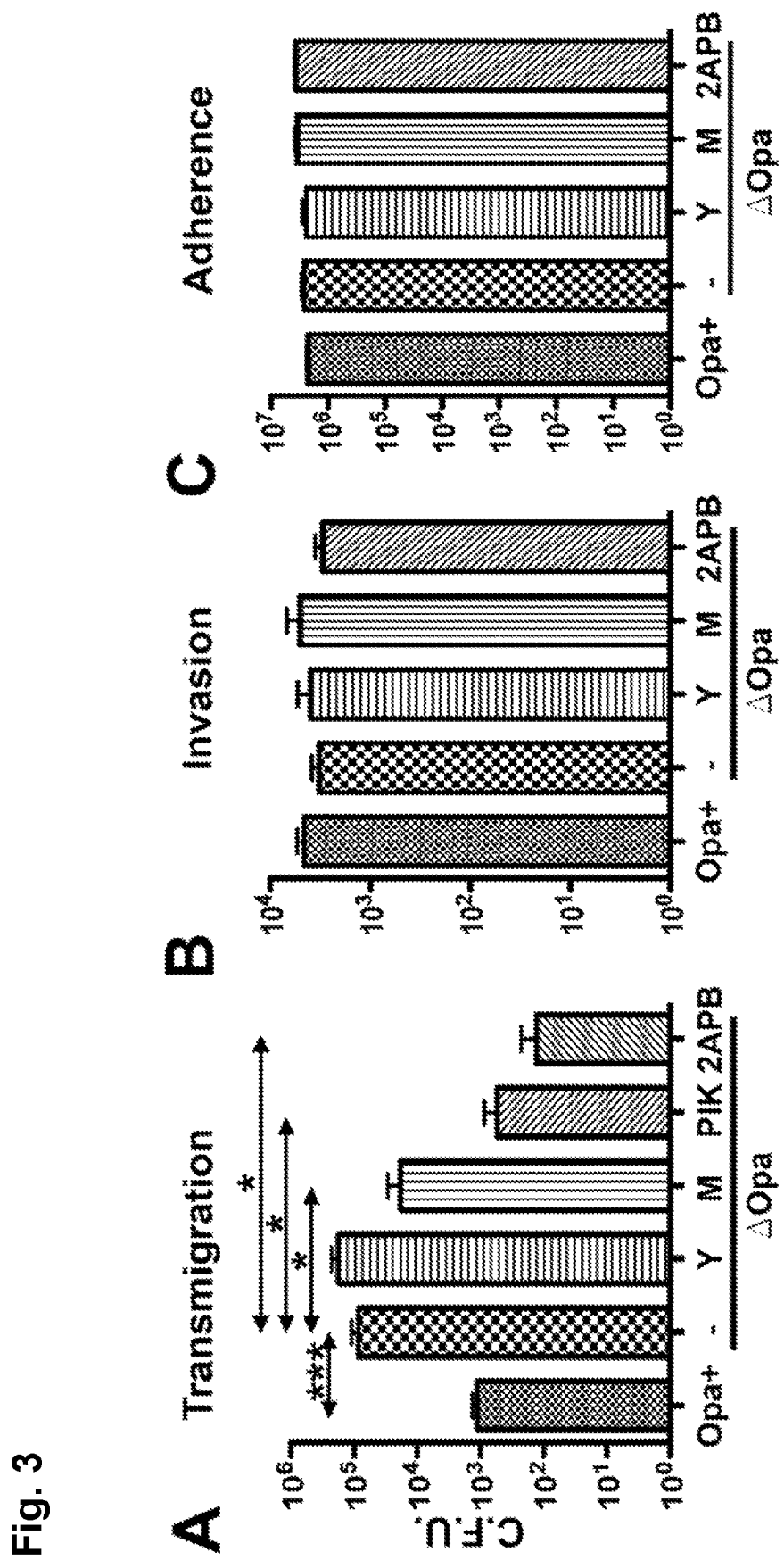
FIG. 3 shows inhibition of $Ca^{2+}$ signal and NMII activation as well as Opa expression reduces Ng penetration into the epithelium but not Ng adherence and invasion. (A-C) Polarized T84 cells were untreated or pre-treated with the ROCK inhibitor Y27632 (Y), the MLCK inhibitors ML-7 (M) and PIK, or the intracellular $Ca^{2+}$ release inhibitor 2APB (10 µM), and apically incubated with MS11Opa+ or ΔOpa for 6 h in the presence or absence of inhibitors. The basal medium was collected to determine transmigrated Ng (A). Invaded Ng (B) and adhered Ng (C) were quantified by the gentamicin resistance assay. (D and E) Polarized HEC-1-B cells were apically incubated with MS11Opa+ or ΔOpa for 6 h, and the numbers of transmigrated (D) and adhered Ng (C) were determined as described above. Shown are the means (±SD) of >6 transwells from 4-6 independent experiments. (F and G) Human endocervical tissue explants were incubated with MS11ΔOpa for 24 h in the presence or absence of ML-7 and PIK, stained for ZO-1, nuclei and Ng, and analyzed by 3D-CFM (F). Ng subepithelial penetration (arrows) was quantified using 3D-CFM images as the percentage of epithelial cells with basal Ng staining among the total number of Ng associated epithelial cells (G). Shown are the average values (±SD) of >50 epithelial cells of endocervical tissue explants from two to three human subjects. *$p \leq 0.001$; $p \leq 0.01$; *$p \leq 0.05$.
Figure 3:
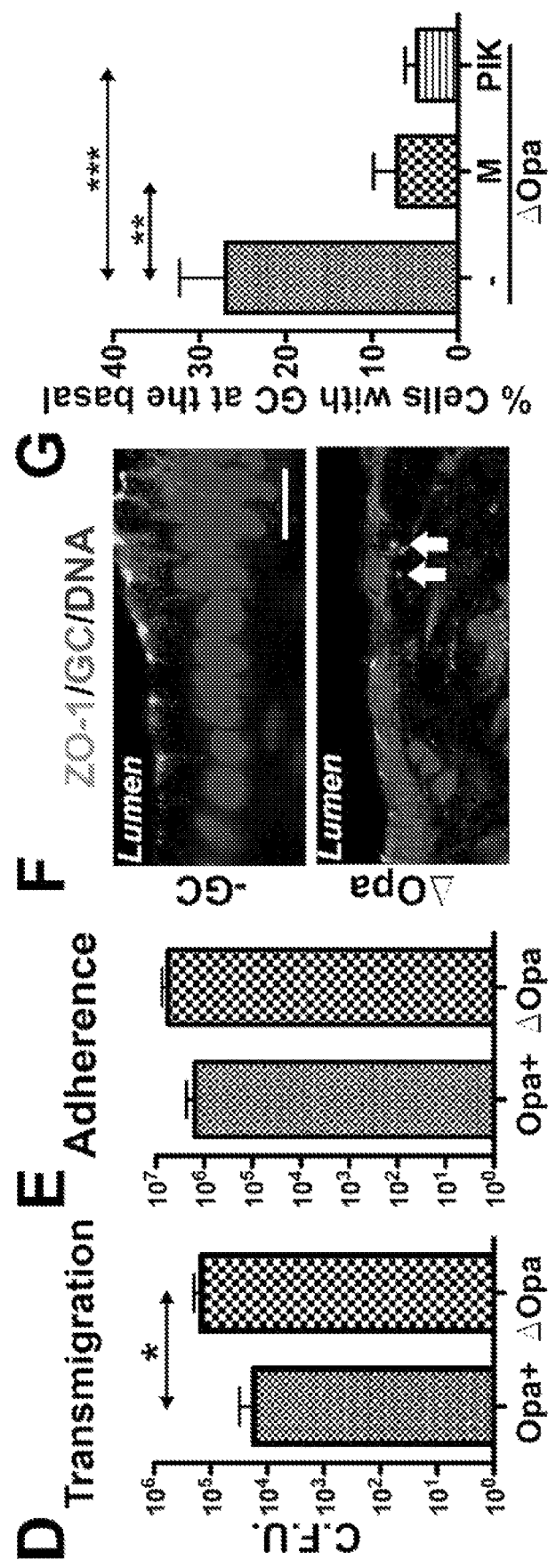
Figure 12:
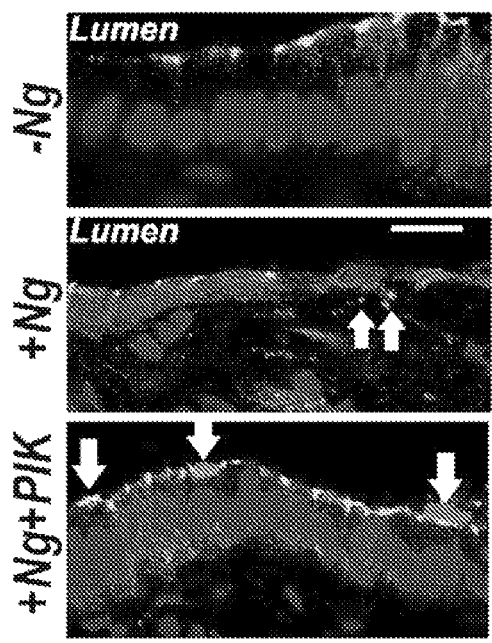
FIG. 12 shows the MLCK inhibitor PIK inhibits Ng penetration into human endocervical epithelia (A-B) and Ng trans-migration across polarized human epithelial cells (C).
Figure 12:
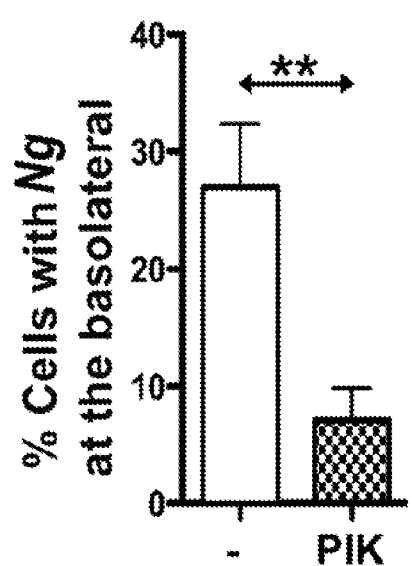
Figure 12:
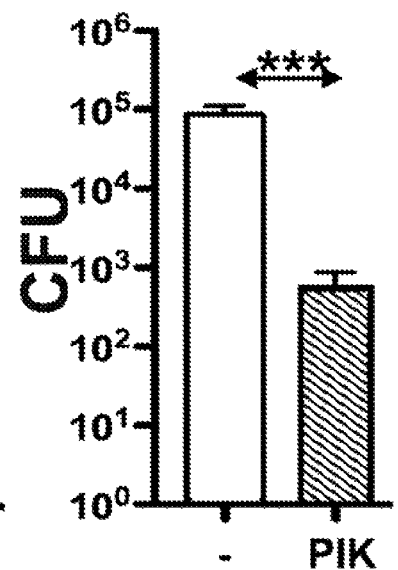
Figure 13:
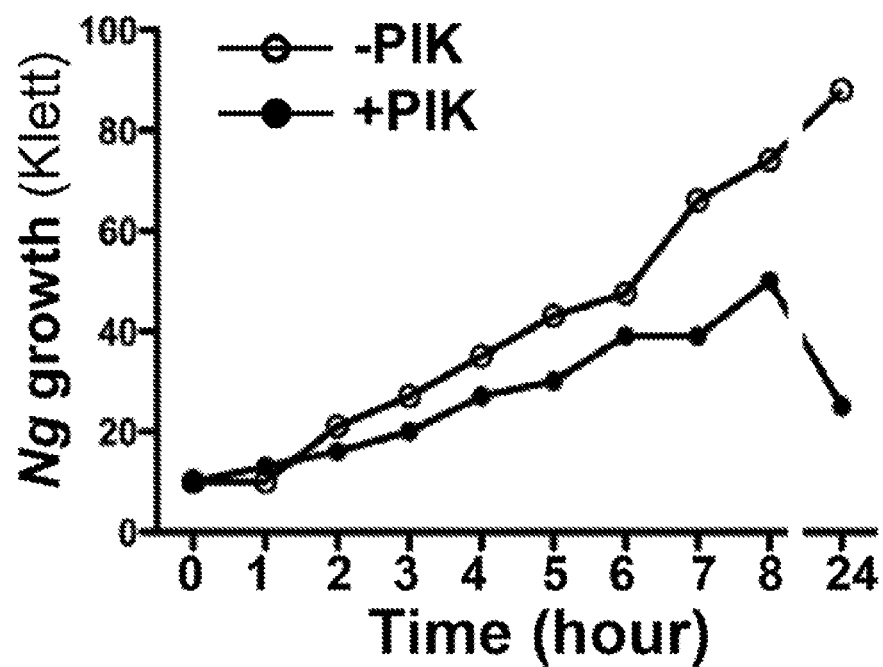
FIG. 13 shows the MLCK inhibitor PIK suppresses Ng growth.

Aspects of the disclosure are illustrated by demonstrating that PIK and ML-7 can prohibit Ng from damaging the epithelial barrier and penetrating into human cervical tissues, which are important steps for Ng to establish penetrating infection (FIGS. 3 and 12). In addition, the disclosure demonstrates that PIK suppresses Ng growth (FIG. 13).

Compositions of this disclosure comprise PIK and/or ML-7 and additional components that are not particularly limited, other than a requirement that the composition be suitable for intravaginal administration. Thus, in embodiments the disclosure comprises contacting the vaginal epithelium directly with PIK, and as such PIK can be combined with a wide variety of components and provided in numerous formulations/delivery devices. Any form of drug delivery system which will effectively deliver PIK and/or ML-7 to the vaginal epithelium and mucosa is included within the scope of this invention.

In certain embodiments the disclosure comprises a vaginal drug delivery device and/or system which provides a sustained delivery of PIK and/or ML-7 to the vaginal epithelium and mucosa. The delivery system can comprise any suitable device including but not necessarily limited to a tampon applicators formed from molded plastic, tampons, tampon-like devices, vaginal rings, diaphragms, cervical cups or vaginal sponges. Such devices can include PIK in any suitable formulation, such as a paste, cream, ointment, microcapsules, solution, powder, or gel, etc. In some examples the PIK and/or ML-7 formulation will have a sufficient thickness to maintain prolonged vaginal epithelium and mucosa contact. Alternatively, the drug can be incorporated into a coating on a tampon or tampon-like device, sponge, suppository or other absorbent material impregnated with a PIK and/or ML-7 containing solution, lotion, or suspension, which in certain approaches can be shaped into a tampon-fitting device. In certain examples, PIK and/or ML-7 is provided in association with fibrous material, which may be synthetic or natural, and can include but is not limited to rayon, polyester and cotton. PIK and/or ML-7 can be incorporated into sanitary napkins. Thus, the disclosure includes a variety of devices that can be used as applicators of PIK- and/or ML-7-comprising compositions.

PIK and/or ML-7 containing formulations can also be provided separately from a device or as a component of a kit with a device. The formulations can be any suitable compositions which include but are not necessarily limited to gels, hydrogels, creams, ointments, pastes, solutions, etc. In general, in order to achieve desirable compound release such that it can act directly act on or target bacteria on the vaginal epithelium and/or mucosa PIK and/or ML-7 can be included in a pharmaceutical formulation that comprises a pharmaceutically acceptable excipient. Examples of suitable excipients are well known in the art and are described in, for example, Garg S., et al. Compendium of Pharmaceutical Excipients for Vaginal Formulations, Pharmaceutical Technology DRUG DELIVERY (2001), p. 14-24, from which the description of excipients is incorporated herein by reference. Kits contain a composition comprising PIK and/or ML-7, and may further comprise a delivery device for intravaginal administration of the composition comprising PIK and/or ML-7. The composition comprising PIK and/or ML-7 may be provided with the kit as a component of the device, or PIK and/or ML-7 may be provided in a separate container for combining with the device prior to use. Kits can further comprise printed instructions for using the composition/device for intravaginal administration.

Formulations of the invention may comprise mucoadhesive agents to bring the released drug into prolonged, close contact with the mucosal surface. Numerous mucoadhesive agents are known in the art and can be adapted for use in compositions, devices and methods of this disclosure. For example, Kavitha et al., 2011, Novel Mucoadhesive Polymers—A Review, Journal of Applied Pharmaceutical Science 01 (08); 2011: 37-42, describes various mucoadhesives that can be used. In non-limiting examples suitable natural mucoadhesive polymers include tragacanth, sodium alginate, karaya gum, guar gum, xanthan gum, soluble starch, gelatin, pectin, cellulose, chitosan, etc. The mucoadhesive agent can be a cellulose derivative, such as hydroxypropyl methylcellulose.

Other components may be present in the compositions of this invention such as water, anti-oxidants, chelating agents, preservatives, oils, waxes, alcohols, surfactants, emulsifiers, viscosity building agents, solvents, moisturizing agents, solubilizers and the like, antiseptic chemicals, and other specific components, such as propylenes, polypropylenes, polysorbates, and a variety of simple polyol compounds, i.e., glycerol. The relative quantities of such components may vary according to the desired nature and consistency of the composition, including creams, ointments, waxy suppositories, gelatin capsules, anhydrous polymeric suppositories and the like. In certain embodiments buffered forms of the compositions of this invention may be made as emulsions, gels or as two-phase, or dual, dosage forms. In other embodiments, a composition of the disclosure can comprise hydrophilic phase and a hydrophobic phase, wherein PIK and/or ML-7 may be present in the hydrophilic phase due to its water solubility. Any of the compositions or components thereof can be buffered. In certain implementations, a composition or a component of a composition of this disclosure includes a buffer suitable to maintain the pH at a physiological pH, which for intravaginal purposes may be a pH level of from about 3.0 to about 5.5.

In certain embodiments the disclosure provides intravaginal drug delivery devices for delivering PIK and/or ML-7, wherein devices are formed from or comprise biocompatible polymers. The polymers may be in the form of a polymer matrix. In certain aspect PIK and/or ML-7 can be released by diffusion or other processes through the polymer matrix. In certain implementations either or both non-biodegradable and biodegradable polymeric matrices can be used, and such polymers may be natural or synthetic polymers. The polymer is selected based on the period of time over which release is desired, generally in the order of a few hours, a few days, or longer. Non-limiting examples of synthetic polymers which can be used in embodiments of this disclosure include: polyamides, polycarbonates, polyalkylenes, polyvinyls, polysiloxanes, polyurethanes, and synthetic celluloses; natural polymers include but are not limited to alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, and hydrophobic proteins, copolymers and mixtures thereof.

In certain embodiments a composition and/or device comprises a polymeric matrix that may be formed as a gel, and comprises at least one of hydrophilic polymers, hydrophobic polymers, poly(acrylic acids) (PAA), poly(lactic acids) (PLA), carageenans, polystyrene sulfonate, polyamides, polyethylene oxides, cellulose, poly(vinylpyrrolidone) (PVP), poly(vinyl alcohol) (PVA), chitosan, poly (ethylacrylate), methylmethacrylate, chlorotrimethyl ammonium methylmethacrylate, hydroxyapatite, pectin, porcine gastric mucin, poly(sebacic acid) (PSA), hydroxypropyl methylcellulose (HPMC), cellulose acetate phthalate (CAP), magnesium stearate (MS), polyethylene glycol, gum-based polymers and variants thereof, poly (D,L)-lactide (PDLL), polyvinyl acetate and povidone, carboxypolymethylene, and derivatives thereof. In certain aspects the disclosure comprises including PIK in micro- or nanoparticles formed from any suitable biocompatible material, including but not necessarily limited to poly(lactic-co-glycolic acid) (PLGA). Liposomal and microsomal compositions are also included. In certain aspects a gel of this disclosure comprises gel comprises a carbomer, methylparaben, propylparaben, propylene glycol, sodium carboxymethylcellulose, sorbic acid, dimethicone, a sorbitol solution, or a combination thereof. In embodiments a gel of this disclosure comprises one or a combination of benzoic acid, BHA, mineral oil, peglicol 5 oleate, pegoxol 7 stearate, and purified water, and can include any combination of these compositions.

The disclosure includes devices and kits that relate to inserting into vagina an intravaginal medicated device comprising PIK and/or ML-7. In certain embodiments the disclosure provides a vaginal tampon, vaginal ring, vaginal cup, vaginal tablet, vaginal sponge, a vaginal bioadhesive tablet, a vaginal lubricant, a condom, or a modified female hygiene or other vaginal health care product, such as prescription and over-the-counter antifungal products that treat and/or cure vaginal yeast infections, or bacterial vaginosis, but that have been adapted to include PIK and/or ML-7 for prophylaxis and or therapy of Ng infection. Applicators that are provided with female hygiene or vaginal health care products can be adapted for intravaginal administration of PIK and/or ML-7.

In certain aspects a method of the invention comprises intravaginal insertion of a medicated device comprising PIK and/or ML-7. In certain approaches the medicated device is applied, that is, inserted intravaginally once, twice or several times a day, as needed, or according to a treatment regimen. In certain embodiments the device may be provided in dry or wet form or may be wetted prior insertion. The delivery composition can be formulated to adhere to and act directly on the vaginal epithelium and/or mucosa, and such formulations can be provided if desired without components which promote the transport or transfer of PIK and/or ML-7 through the vaginal wall. Thus, in certain approaches PIK and/or ML-7 does not enter the circulatory system of the individual. In certain aspects a composition and/or device of this and may comprise one or more additional agents for treatment of vaginal, fungal, viral, or other bacterial or parasitic infections. Such compositions include but are not limited to antibiotics and anti-viral agents, and chemical compounds that act as biocides or antiseptic agents, such as benzalkonium chloride. Additional agents include but are not limited to soothing compositions that contain, for example anti-irritant and/or anti-inflammatory agents, such as hydrocortisone or related compounds, or emollients, or anti-hemorrhagic or hemostatic or anti-allergic agents.

In embodiments a composition and/or device of this disclosure comprises a contraceptive agent, such as a spermicide or a hormonal or non-hormonal contraceptive drug.

It will be recognized from the foregoing, and without intending to be constrained by any particular theory, it is considered that because PIK targets to a host factor used by Ng to cause gonorrhea, the present disclosure is suitable to combat the rise of antibiotic resistance by reducing infection cases and hence overall antibiotic use. Further, approaches of the present disclosure do not require any significant change in sexual behavior. Moreover, because Ng penetrating infection has a long incubation time (>12 hours), intravaginally applied PIK can remain effective hours after sexual exposure. Thus, the disclosure provides a novel gonorrhea preventative that is expected to be effective, user-friendly and low in side effects.

The following examples are intended to illustrate but not limit the invention.

EXAMPLE 1

This example provides a description of a new ex vivo infection model, human endocervical tissue explants. Using this model and polarized epithelial cells, we revealed links between Ng infectivity, Ng induced exfoliation, apical junction disassembly, and signaling in polarized columnar endocervical epithelial cells, and novel roles of Opa in these events. Ng induce the exfoliation of polarized endocervical epithelial cells through disrupting the apical junction. Opposite to Ng induced shedding of squamous epithelial cells, the exfoliation of columnar epithelial cells does not reduce Ng adherence and invasion; instead, it increases Ng penetration into the subepithelium. Both Ng induced epithelial exfoliation and apical junction weakening require $Ca^{2+}$-dependent redistribution of active NMII. Opa expression inhibits Ng induced exfoliation and junctional disruption by interfering with NMII activation and reorganization without affecting $Ca^{2+}$ flux. The results suggest that Ng modify the exfoliation process for infection by activating Ca+ flux and NMII redistribution in endocervical epithelial cells, and Opa expression controls the magnitude of this process by regulating the levels of NMII activation and redistribution.

Ng-induced epithelial exfoliation from human endocervical tissue explants and polarized monolayers is inhibited by Opa expression. We utilized human endocervical tissue explants and the polarized human colonic epithelial cell line T84 to determine whether Ng infected polarized epithelial cells undergo exfoliation. Tissue explants that were cultured with the mucosal side up and T84 cells that were polarized on transwells were inoculated apically with a Ng strain, MS11 that express phase variable Opa and pili (MS11Opa+) at a MOI of ~10 for 6 or 24 h. Thin sections of cryopreserved endocervical tissues and T84 cells were stained with a DNA dye and Ng specific polyclonal antibodies and analyzed using and three-dimensional confocal fluorescence microscopy (3D-CFM). Images showing both the mucosal and subepithelial sides of the endocervix and T84 monolayers were analyzed. Epithelial cells at the top of the endocervical epithelium of tissue explants or T84 monolayers, indicated by white lines, were counted as exfoliating cells (FIG. 1A) and quantified as the percentage of total Ng associated cells. After 24 h incubation, the exfoliation of Ng associated epithelial cells was significantly increased in both the endocervical epithelium (FIGS. 1B and 1C) and the T84 monolayer (FIGS. 1D and 1E), compared to uninfected controls. This indicates that polarized T84 monolayers behave similarly to the endocervical epithelium upon Ng infection. There was no significant increase in the percentage of Ng associated epithelial cells exfoliated from T84 monolayer after 6-h inoculation, compared to uninfected cells (FIG. 1E, left panel).

To determine if Opa has a role in the exfoliation of columnar epithelial cells, we inoculated endocervical tissue explants and polarized epithelial cells with MS 11ΔOpa, a Ng strain where all 11 opa genes were deleted. MS11ΔOpa increased the percentage of epithelial exfoliation from 32.3% to 66.3% in tissue explants (FIGS. 1B and 1C) and from 31.2% to 55.8% in T84 monolayers (FIGS. 1D and 1E). Even at 6 h, MS11ΔOpa-infected T84 cells exfoliated significantly more than the uninfected control (FIGS. 1D and 1E). These results indicate that Ng induces the epithelial exfoliation from the endocervix and cell line-formed polarized monolayers, and Opa expression inhibits the exfoliation.

Figure 2:
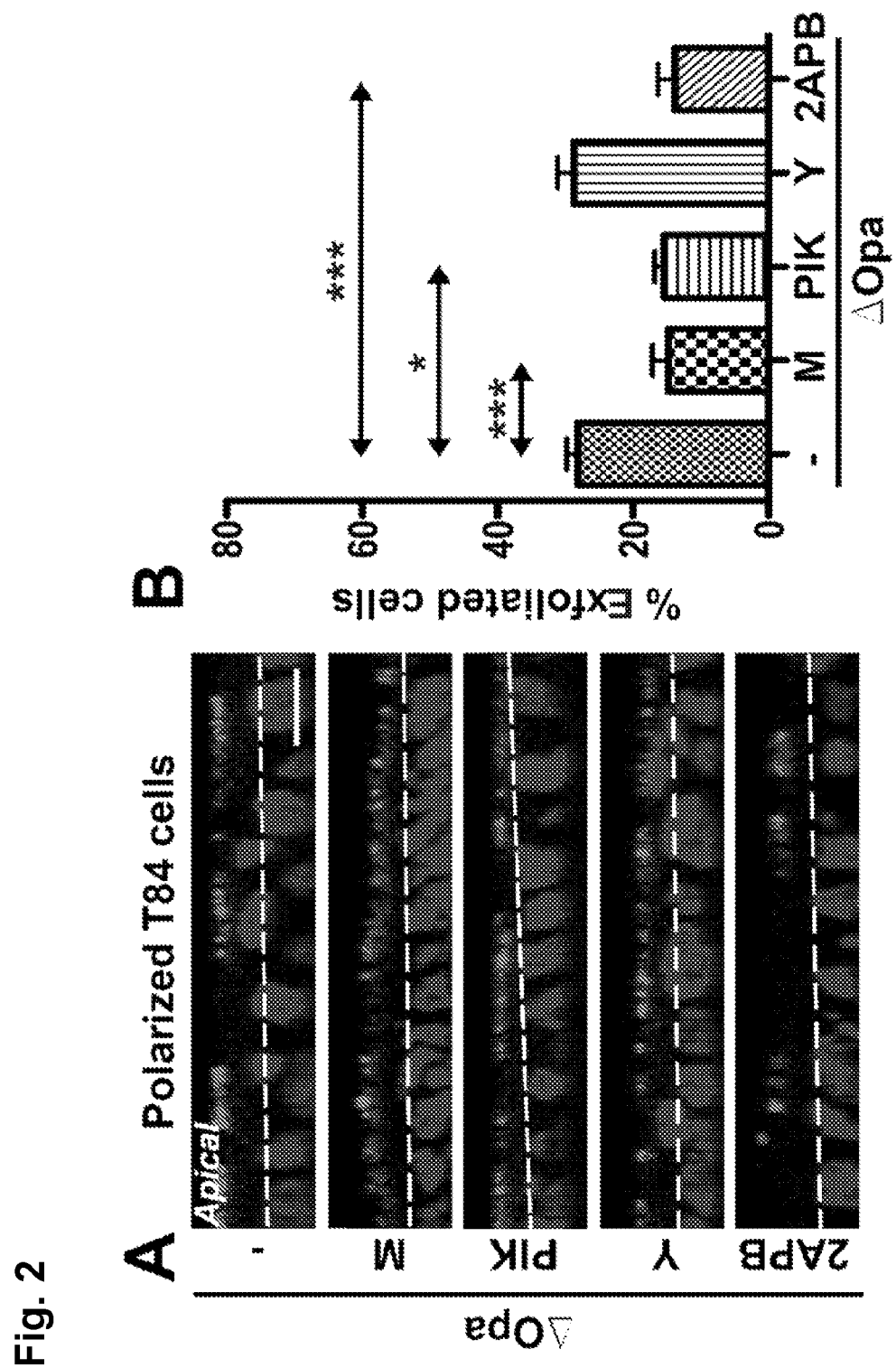
FIG. 2 shows Ng induces exfoliation of polarized epithelial cells requires the activation of $Ca^{2+}$ flux and non-muscle myosin II (NMII) by myosin light chain kinase (MLCK). Polarized T84 cells (A and B) and human endocervical tissue explants (C and D) were untreated or pre-treated with the ROCK inhibitor Y27632 (Y, 10 µM) or the MLCK inhibitors ML-7 (M, 10 µM) or PIK (100 µM) for 1 h and apically incubated with MS11Opa+ or ΔOpa for 6 or 24 h in the presence or absence of inhibitors. Cells were fixed, stained for DNA and Ng, and analyzed using 3D-CFM. Shown are representative images (Scale bar, 10 µm) (A and C). The average percentages (±SD) of exfoliated cells were determined as FIG. 1 from >15 randomly selected fields (>50 cells) of three independent experiments or cervixes of two to three human subjects. *$p \leq 0.001$; $p \leq 0.01$; *$p \leq 0.05$.
Figure 2:
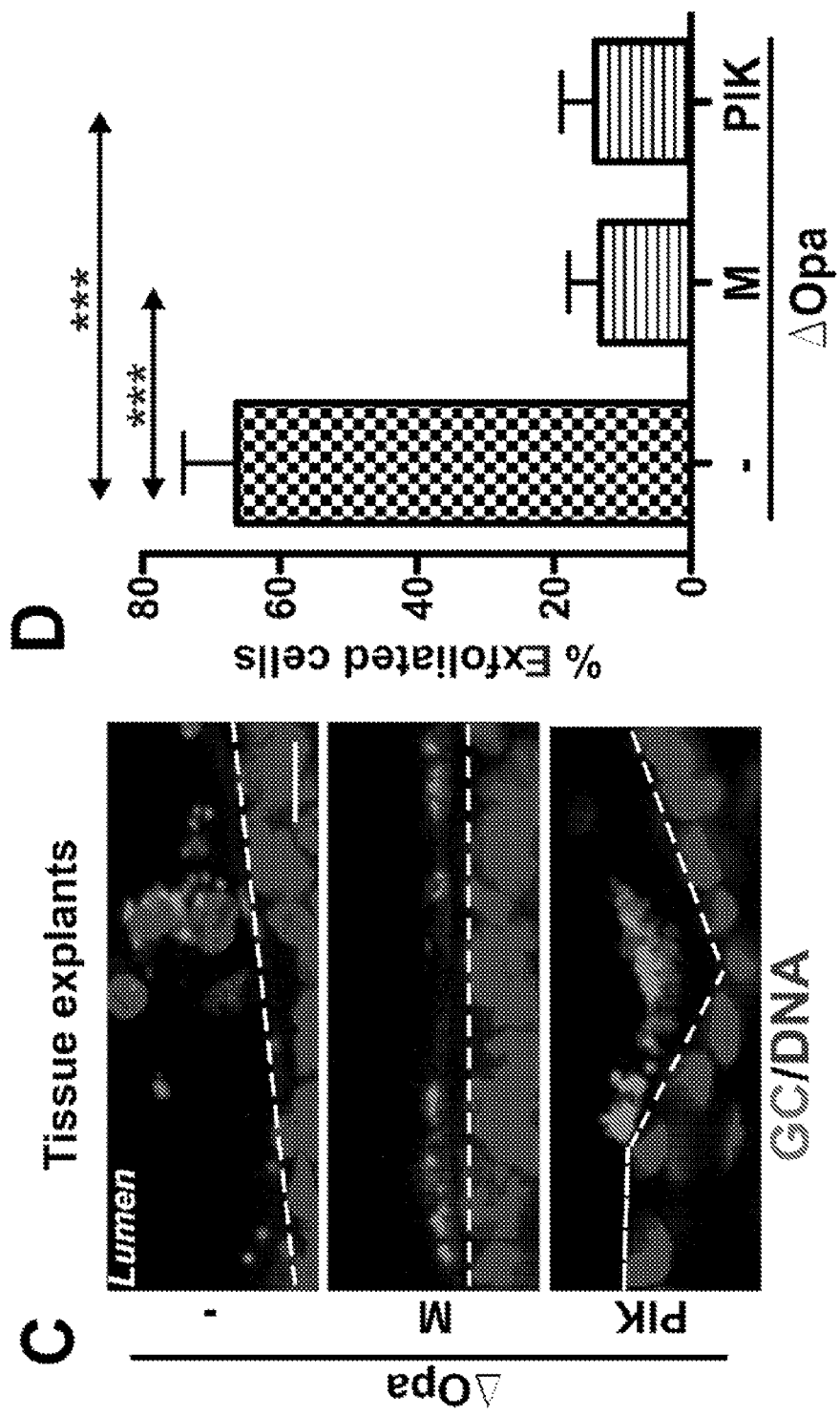
Figure 8:
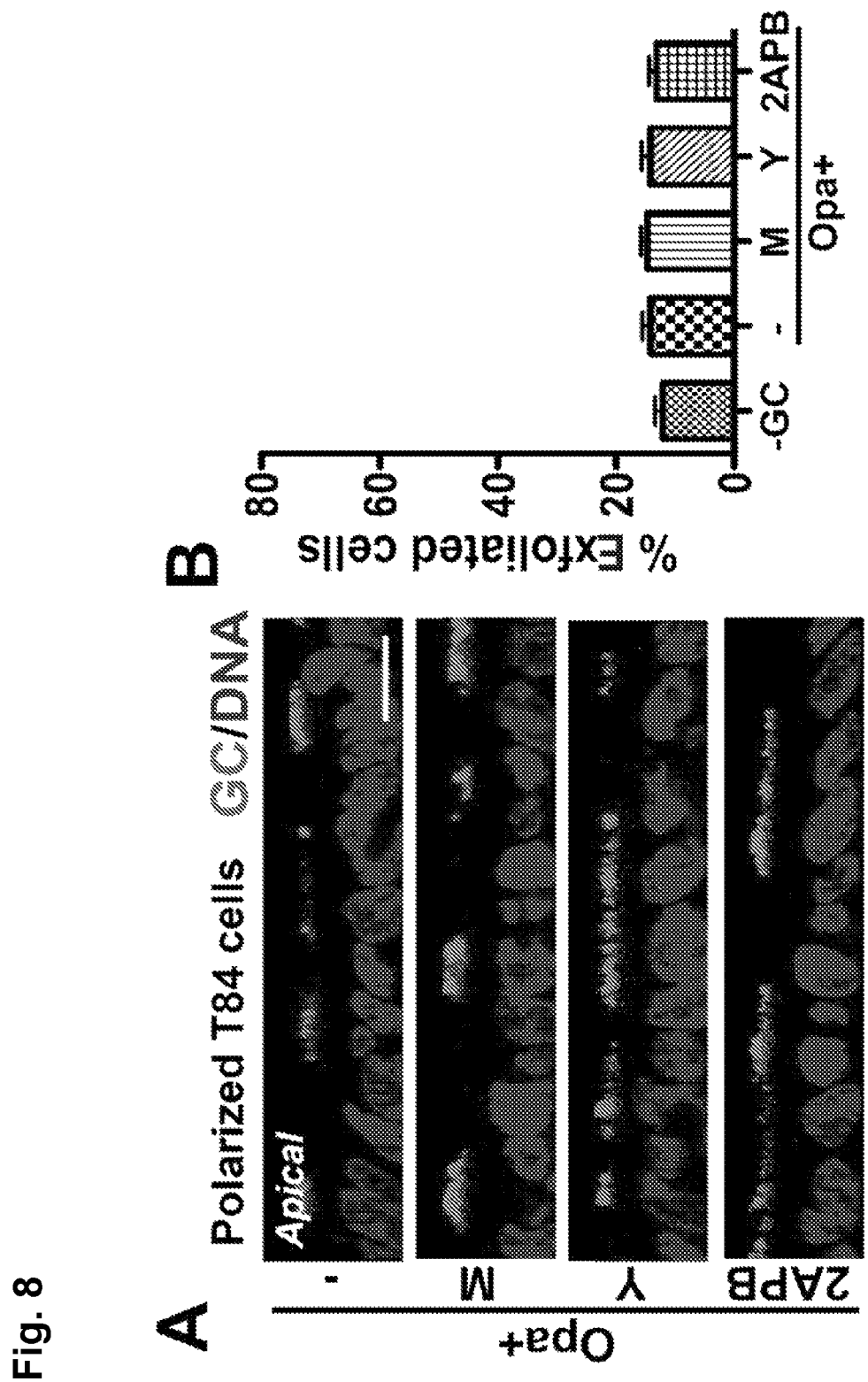
FIG. 8 shows the effects of inhibitors of $Ca^{2+}$ flux and NMII phosphorylation on epithelial exfoliation induced by Opa-expressing Ng. Polarized T84 cells on transwells were untreated or pre-treated with the ROCK inhibitor Y27632 (Y), the MLCK inhibitors ML-7 (M), and an inhibitor of $Ca^{2+}$ release from intracellular pools, 2APB, for 1 h and apically incubated with MS11Opa+ for 6 h in the presence or absence of inhibitors. Cells were fixed, stained for DNA and Ng, and analyzed using 3D-CFM. Shown are representative images that intercept both the apical and basolateral surfaces (Scale bar, 10 μm) (A). Based on cell nuclear staining, the average percentage (±SD) of exfoliated epithelial cells was determined by counting the number of Ng positive epithelial cells localizing above the epithelium of T84 monolayers versus the total number of Ng associated cells in randomly selected fields. Shown are the results from >15 randomly selected fields (>50 individual cells) from three independent experiments. (B) Graph showing percentage of exfoliated cells.

Ng-induced epithelial exfoliation depends on the activation of non-muscle myosin II and $Ca^{2+}$ flux. To determine if Ng induced exfoliation of endocervical epithelial cells depends on NMII, we inhibited the activation of NMII using inhibitors specific for Rho-associated kinase (ROCK), Y27632, and myosin light chain kinase (MLCK), ML-7 and PIK. Polarized T84 cells and human endocervical tissue explants were treated with individual inhibitors for 1 h before and during incubation with Ng. We found that both the small chemical inhibitor (ML-7) and the catalytic site-targeted peptide inhibitor (PIK) of MLCK reduced the exfoliation of MS11ΔOpa-infected (FIGS. 2A and 2B) but not MS11Opa+-infected epithelial cells from T84 monolayers (FIG. 8). In contrast, treatment with the ROCK inhibitor did not significantly change the percentage of epithelial exfoliation, no matter if epithelial cells were infected with MS11Opa+ (FIG. 8) or MS11ΔOpa (FIGS. 2A and 2B). Importantly, the treatment of MLCK inhibitor, ML-7 or PIK, also decreased the epithelial exfoliation of human endocervical tissue explants to the basal level (FIGS. 2C and 2D).

Figure 9:
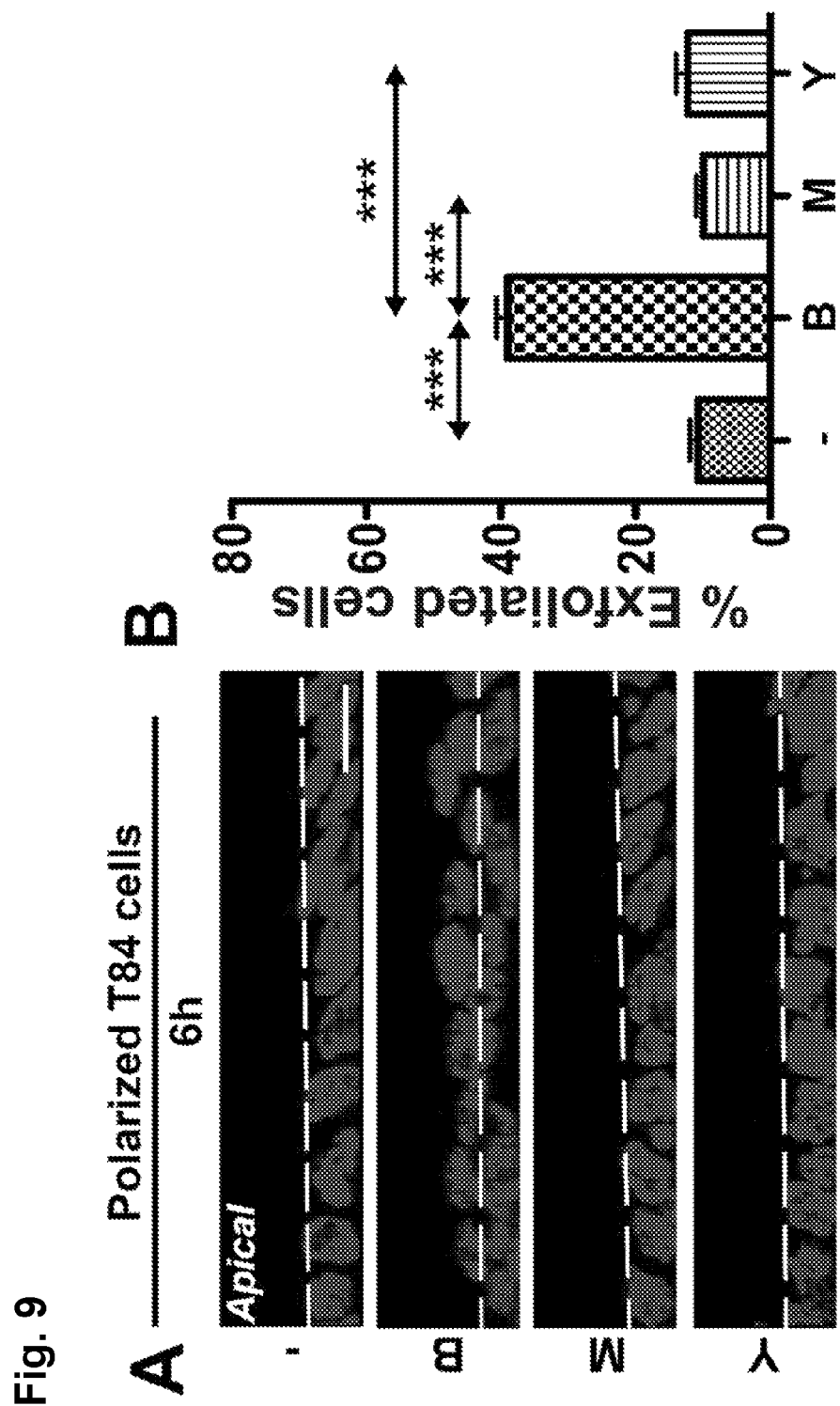
FIG. 9 shows treatment of the NMII motor inhibitor blebbistatin, but not the MLCK inhibitors ML-7 and PIK or the $Ca^{2+}$ inhibitor 2APB induces the exfoliation of polarized T84 cells in the absence of Ng. Polarized T84 cells were treated with inhibitors for 6 h, fixed, stained to visualize the cell nuclei, and imaged by 3D-CFM. The percentage of cell moving above the epithelial monolayer (dash lines) was determined from three independent experiments. Scale bar, 5 μm. *$p \leq 0.05$.

As MLCK activation requires $Ca^{2+}$-bound calmodulin and the MLCK inhibitor PIK blocks the calmodulin-binding site in MLCK, we investigated if Ng induced exfoliation of polarized epithelial cells depends on $Ca^{2+}$ flux. We utilized 2APB, an inhibitor that blocks $Ca^{2+}$ release from intracellular stores. Treatment with 2APB also reduced the exfoliation of polarized T84 cells to the level similar to ML-7 and PIK (FIGS. 2A and 2B). As controls, we treated polarized T84 cells with the inhibitors alone, and found that ML-7, PIK, and 2APB did not affect epithelial exfoliation, but the NMII motor inhibitor blebbistatin increased epithelial exfoliation without Ng inoculation (FIG. 9). These results suggest that Ng induce exfoliation of polarized epithelial cells via $Ca^{2+}$- and MLCK- but not ROCK-dependent activation of NMII.

Opa and $Ca^{2+}$/NMII regulate Ng penetration into polarized epithelial cells oppositely but have no effect on Ng adherence. We have previously shown that Opa expression inhibits Ng transmigration across polarized epithelial cells in addition to reducing epithelial exfoliation shown here. These findings implicate a relationship between epithelial exfoliation and Ng transmigration. To investigate this relationship, we determined whether inhibiting Ng induced exfoliation by MLCK and $Ca^{2+}$ inhibitors would affect the ability of Ng to adhere to, invade into, and transmigrate across polarized epithelial cells. Consistent with what we previously reported, MS11ΔOpa transmigrated from the apical surface of polarized T84 cells into the basolateral chamber in a much greater number than MS11Opa+ (FIG. 3A), but adhered and invaded at similar levels as MS11Opa+ (FIGS. 3B and 3C). Similarly, MS11ΔOpa transmigrated across polarized HEC-1-B cells, a human endometrial epithelial line, more efficiently than MS11Opa+ (FIG. 3D), but adhered similarly as MS11Opa+ (FIG. 3E). These data indicate that Opa-mediated inhibition of epithelial exfoliation does not enhance Ng adherence to polarized epithelial cells, opposite to what was seen in non-polarized epithelial cells.

Inhibition of Ng induced exfoliation by the $Ca^{2+}$ (2APB) and MLCK inhibitors (ML-7 and PIK) significantly reduced the transmigration of MS11ΔOpa across the polarized T84 monolayer (FIG. 3A). However, none of these inhibitors had any significant effect on the adherence and invasion of MS11ΔOpa (FIGS. 3B and 3C). The ROCK inhibitor that did not affect Ng induced exfoliation also had no impact on Ng adherence, invasion and transmigration (FIG. 3A-C). Treatment with the inhibitors alone affected neither the barrier function of the epithelium nor Ng growth. In addition to the increases in Ng transmigration across polarized T84 and HEC-1-B cells, we also detected 27% of bacteria-associated endocervical epithelial cells exhibiting Ng staining on their basal sides in the human tissue explants (FIG. 3F, arrows) after a 24-h inoculation with MS11ΔOpa (FIG. 3G), indicating Ng penetration into the endocervical epithelium and subepithelium. Similar to the results obtained from polarized T84 cells, treatment with either ML-7 or PIK decreased the percentage of epithelial cells with basally associated Ng from 27% to 7.1% (FIG. 3G), significantly inhibiting Ng penetration into the endocervical epithelium. Our results suggest that $Ca^{2+}$ flux and the activation of NMII by MLCK in polarized epithelial cells, which are required for Ng induced epithelial exfoliation, also are critical for Ng transmigration across and penetration into the human endocervical epithelium, but not for Ng adherence and invasion.

Figure 4:
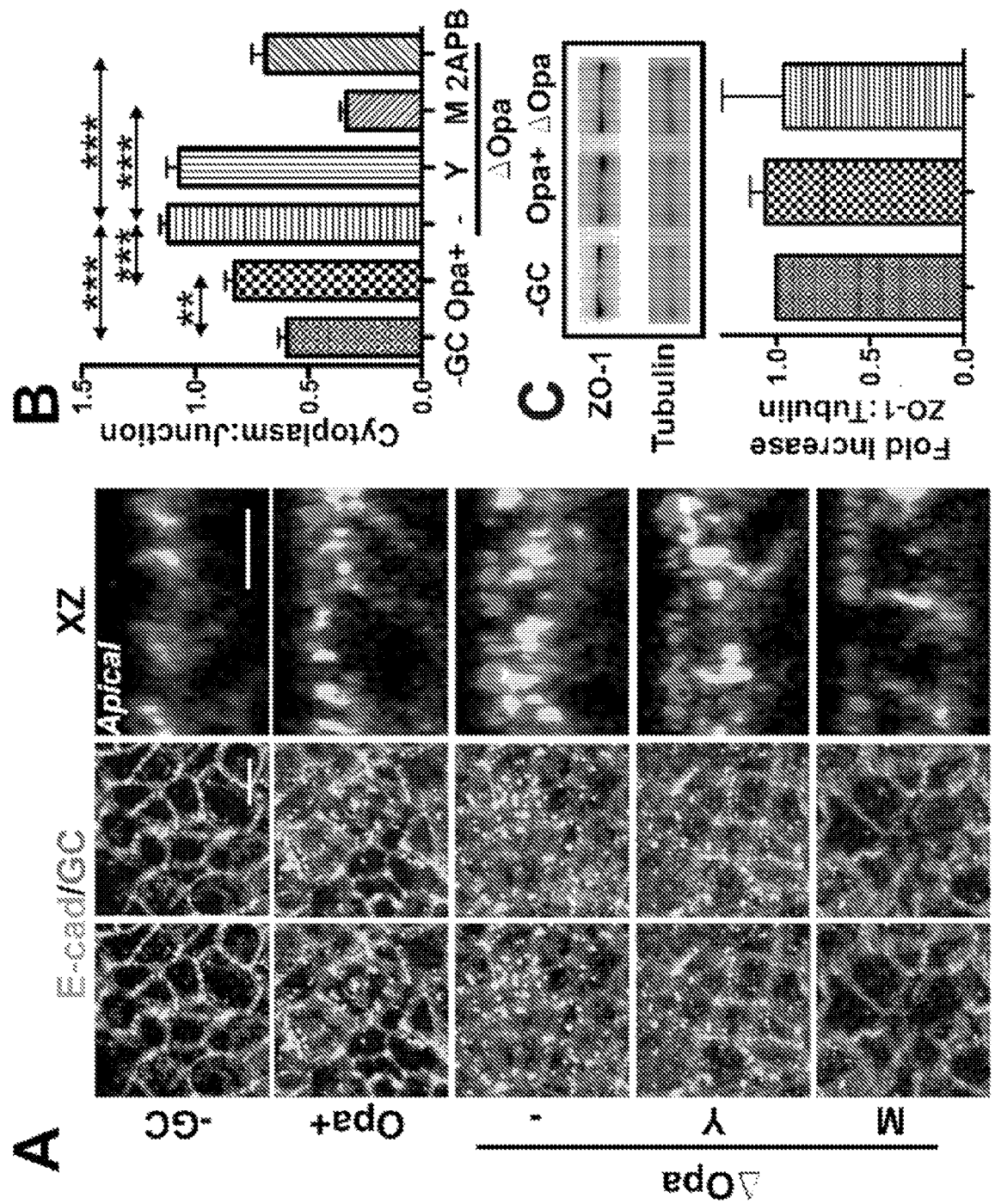
FIG. 4 shows Ng induce apical junction disruption in polarized epithelial cells and endocervical tissue explants in a $Ca^{2+}$- and MLCK-dependent manner. (A and B) Effects of NMII kinase and $Ca^{2+}$ inhibitors on the distribution of E-cadherin. Polarized T84 cells were untreated or pre-treated with NMII kinase inhibitors, Y27632 (Y) and ML-7 (M), or a $Ca^{2+}$ inhibitor, 2APB, and then apically incubated with MS11Opa+ or ΔOpa for 6 h in the presence or absence of inhibitors. Cells were fixed, stained for E-cadherin (E-Cad) and Ng, and analyzed using 3D-CFM (A). The average fluorescence intensity ratios (FIR) (±SD) of E-Cad staining at the cytoplasmic to the cell-cell junctional region was determined from >50 cells of three individual experiments using the NIH ImageJ software (B). (C) The expression levels of ZO1 in MS11Opa+- or ΔOpa-infected T84 cells were compared using Western blotting and quantified by the average fold of increases (±SD) in the ratio of ZO1 to tubulin in cell lysates from three independent experiments. (D-F) Effects of MLCK and $Ca^{2+}$ inhibitors on the membrane lateral movement over the apical junction. Polarized T84 cells treated with inhibitors as above were apically inoculated with fluorescently labeled Ng for 4 h and basolaterally stained with CellMask for 15 min (D). Time lapse xz images were acquired using CFM. Shown are representing images (E) and the average percentage (±SD) of cells showing the basolaterally stained dye moving over to the apical surface (F) from >50 randomly selected cells of three independent experiments. Scale bar, 5 µm. (G-H) Effects of Ng and the MLCK inhibitor ML-7 on the ZO1 distribution in human endocervical tissue explants. The tissue explants were untreated or pre-treated with ML-7 (M) for 1 h and incubated with MS11ΔOpa for 24 h in the absence or presence of ML-7. Tissues were stained for ZO1, DNA, and Ng. Shown are representative CFM (G, left panels, arrows to Ng) and 3D reconstituted images (G, right panels) (Bar, 10 µm), and the average percentages (±SD) of Ng associated cells showing continuous ZO1 staining at the apical region (H), from >15 randomly selected fields (>50 cells) from cervixes of two to three human subjects. *$p \leq 0.001$; $p \leq 0.01$; *$p \leq 0.05$. (I) Representative CFM images of ZO1 distribution in exfoliating and surrounding epithelial cells (arrows) of cervical tissues from 4 human subjects.
Figure 4:
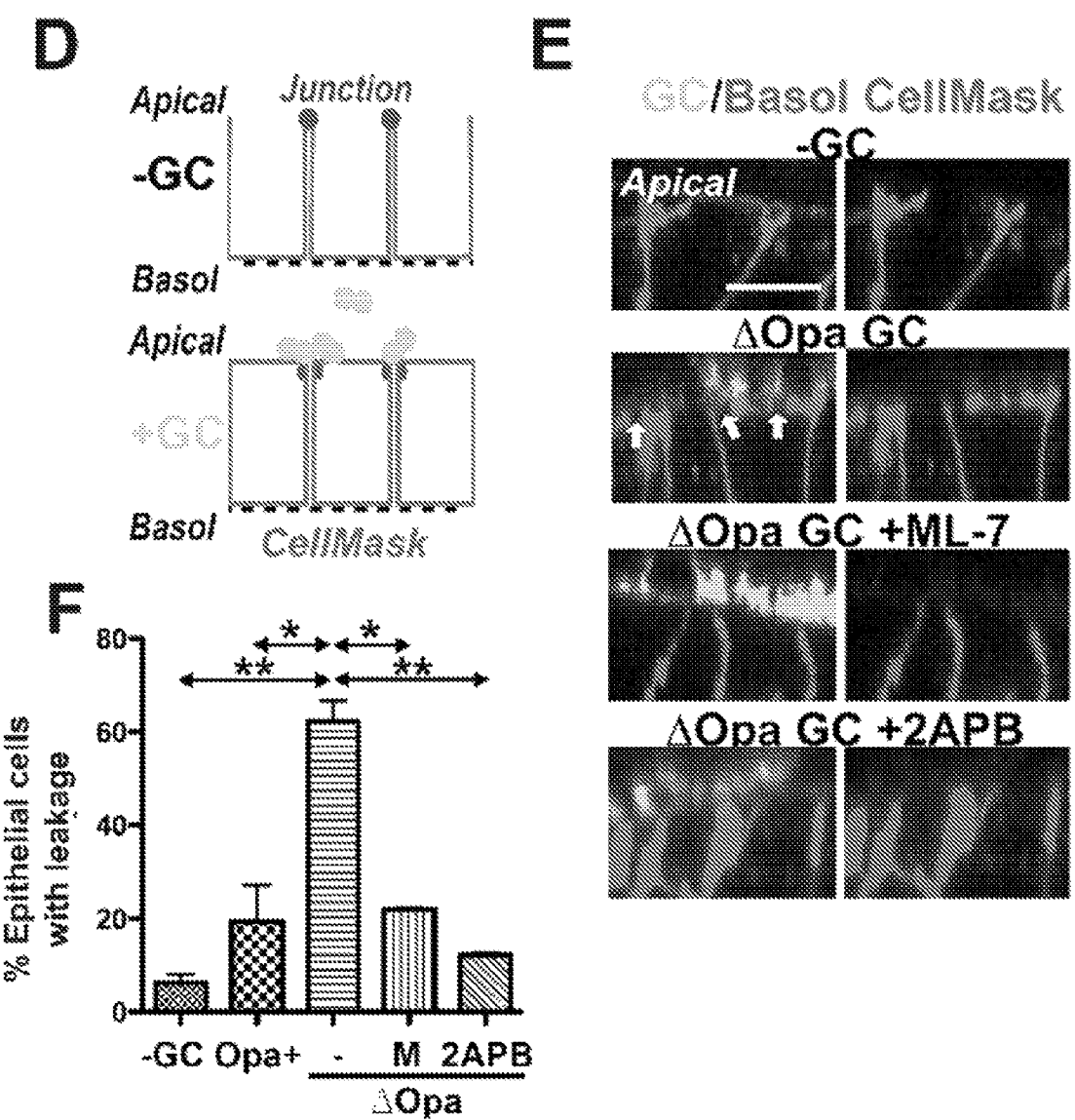
Figure 4:
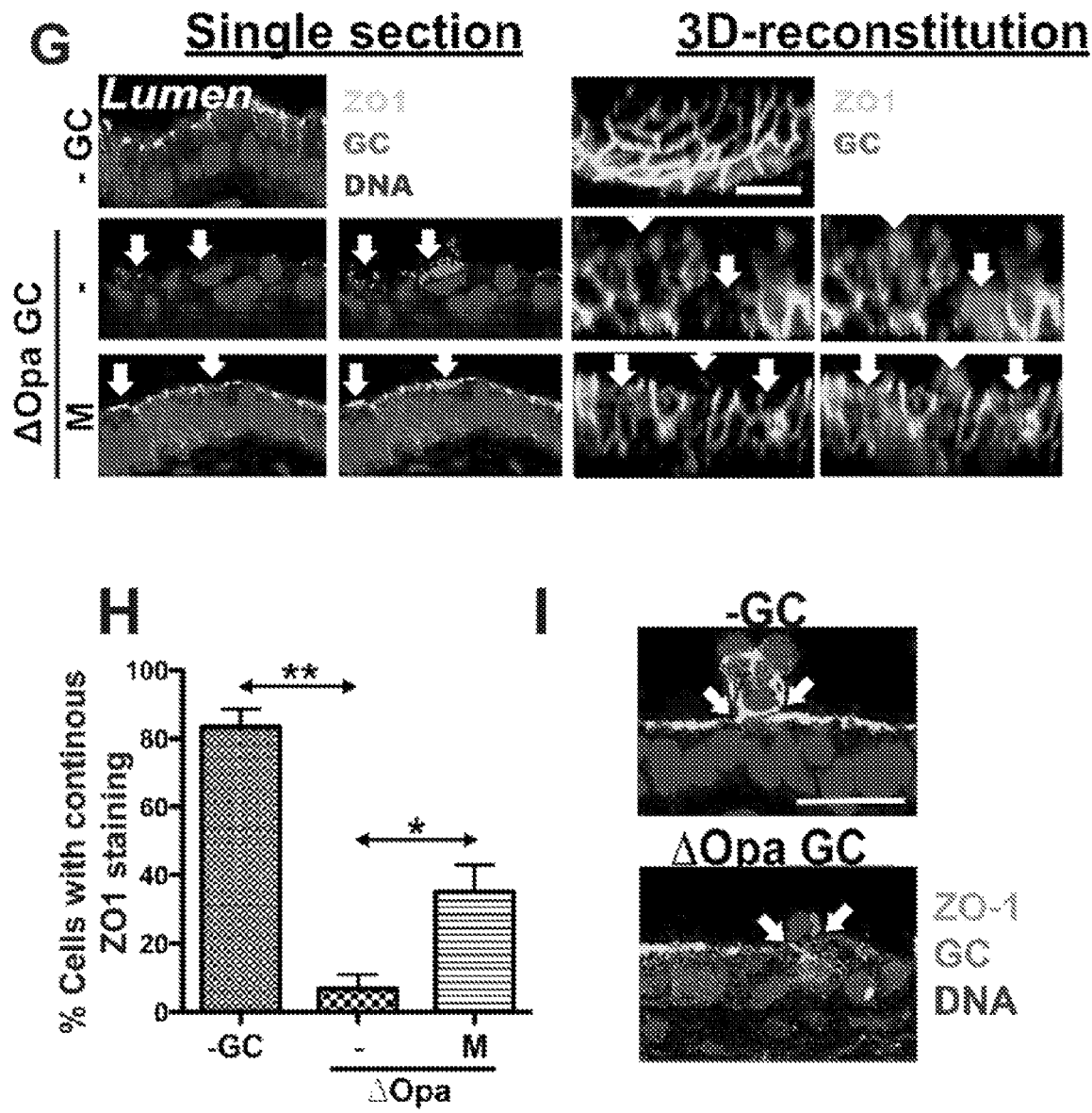

Ng-induced junction disassembly requires NMII activation and $Ca^{2+}$ flux but is suppressed by Opa. The linkage between the efficiency of Ng penetration into the epithelium with Ng induced epithelial exfoliation and apical junction disruption shown here and previously implicate Ng induced junction disruption as an underlying cause of epithelial exfoliation. To test this hypothesis, we determined whether Opa expression and the MLCK and $Ca^{2+}$ inhibitors, which all inhibited Ng induced epithelial exfoliation, also prevent Ng from disrupting the apical junction. The structural integrity of the apical junction was evaluated by analyzing the distribution of E-cadherin using immunofluorescence (IFM) and 3D-CFM and quantifying the fluorescence intensity ratio (FIR) of E-cadherin at the cytoplasm to that at the apical junction. In polarized T84 cells that were not inoculated with Ng, E-cadherin staining was primarily localized at the apical junction (FIG. 4A, top panels). Incubation with Ng changed the continuous E-cadherin staining at the apical junction into puncta in the cytoplasm, indicating endocytosis of E-cadherin (FIG. 4A). This led to a significant increase in the cytoplasm:junction FIR of E-cadherin in both MS11Opa+ and MS11ΔOpa-inoculated epithelial cells, compared to non-inoculated controls (FIG. 4B). In particular, the magnitude of the increase in the FIR was significantly greater in MS11ΔOpa-infected than MS11Opa+-infected epithelial cells (FIG. 4B). Our Western blot analysis did not find any significant changes in the protein level of the apical junctional protein ZO1 between epithelial cells inoculated with MS11Opa+, MS11ΔOpa, and no Ng (FIG. 4C). These results suggest that Opa expression suppresses Ng induced apical junction disassembly by inhibiting E-cadherin endocytosis.

We used inhibitors to determine the role of NMII and $Ca^{2+}$ flux in Ng induced junction disassembly. Treatment with the MLCK inhibitor ML-7 and the $Ca^{2+}$ inhibitor 2APB, but not the ROCK inhibitor Y27632, decreased the punctuate staining of E-cadherin in the cytoplasm and the cytoplasm:junction FIR of E-cadherin to or below the control level in epithelial cells without Ng inoculation (FIGS. 4A and 4B). Thus, $Ca^{2+}$/MLCK inhibitors suppress Ng induced junction disassembly.

Ng-induced junctional disassembly leads to a significant increase in the lateral diffusion between the apical and basolateral membrane but not in the permeability of epithelial monolayers. To determine whether Opa, MLCK and Ca$^{2+}$ flux are involved in this functional alteration of the apical junction, we stained the basolateral surface of polarized T84 epithelial cells exclusively with CellMask dye for 5 min, after apical incubation with fluorescently labeled Ng for 6 h. The appearance of basolaterally stained CellMask dye in the apical membrane indicates a decrease in the fence function of the apical junction (FIG. 4D). In control cells where no Ng were added, <10% of the cells showed the CellMask staining at the apical surface. The percentage of cells with basolaterally labeled CellMask reaching the apical surface increased to 19.4% when MS11Opa+ was inoculated and to 62.2% when MS11ΔOpa was inoculated (FIGS. 4E and 4F). These results indicate that while both Opa+ and ΔOpa Ng decrease the fence function of the apical junction, MS11ΔOpa caused a greater reduction than MS11Opa+. Moreover, the treatment with the MLCK inhibitor ML-7 or the Ca$^{2+}$ inhibitor 2APB significantly lowered the percentage of epithelial cells with the CellMark staining leaked to the apical surface (FIGS. 4E and 4F), thereby inhibiting the Ng induced fence function reduction.

We determined if MS11ΔOpa can induce the disruption of the apical junction in human endocervical tissue. Sections of uninfected and infected tissue explants were stained for the junctional protein ZO1, Ng, and DNA and analyzed by 3D-CFM (FIG. 4G). We quantified junction disruption by determining the percentage of Ng associated epithelial cells that lost continuous apical staining of ZO1, using 3D reconstituted confocal images (FIG. 4G, right panels). After a 24-h incubation with MS11ΔOpa, ZO1 staining at the apical junction of Ng associated epithelial cells appeared to be reduced (FIG. 4G, left panels), and 93.2% of Ng associated epithelial cells showed defective ZO1 staining (FIG. 4G, right panels, arrows), compared to 16.7% of uninfected cells (FIG. 4H). In contrast to the recruitment of ZO1 to epithelial cells neighboring exfoliating cells in uninfected monolayers, no accumulation of ZO1 staining was observed around Ng infected exfoliating cells (FIG. 4I, arrows). Furthermore, Ng inoculation significantly changed the morphology of endocervical epithelial cells, with the cells losing their tall and columnar shape (FIG. 4G, left panels). Treatment with the MLCK inhibitor ML-7 restored both the morphology (FIG. 4G left panels) and apical distribution of ZO1 (FIG. 4H). These data confirm the ability of Ng to compromise the apical junction of the endocervical epithelial cells in a NMII-dependent manner in the human tissue explants.

These results together show that both Opa expression and Ca$^{2+}$/MLCK inhibitors suppress Ng induced disruption of the apical junction, indicating that similar to Ng induced epithelial exfoliation, Ca$^{2+}$ signal and MLCK-mediated NMII activation are required for Ng induced apical junction disruption while Opa expression inhibits the junction disruption.

Figure 5:
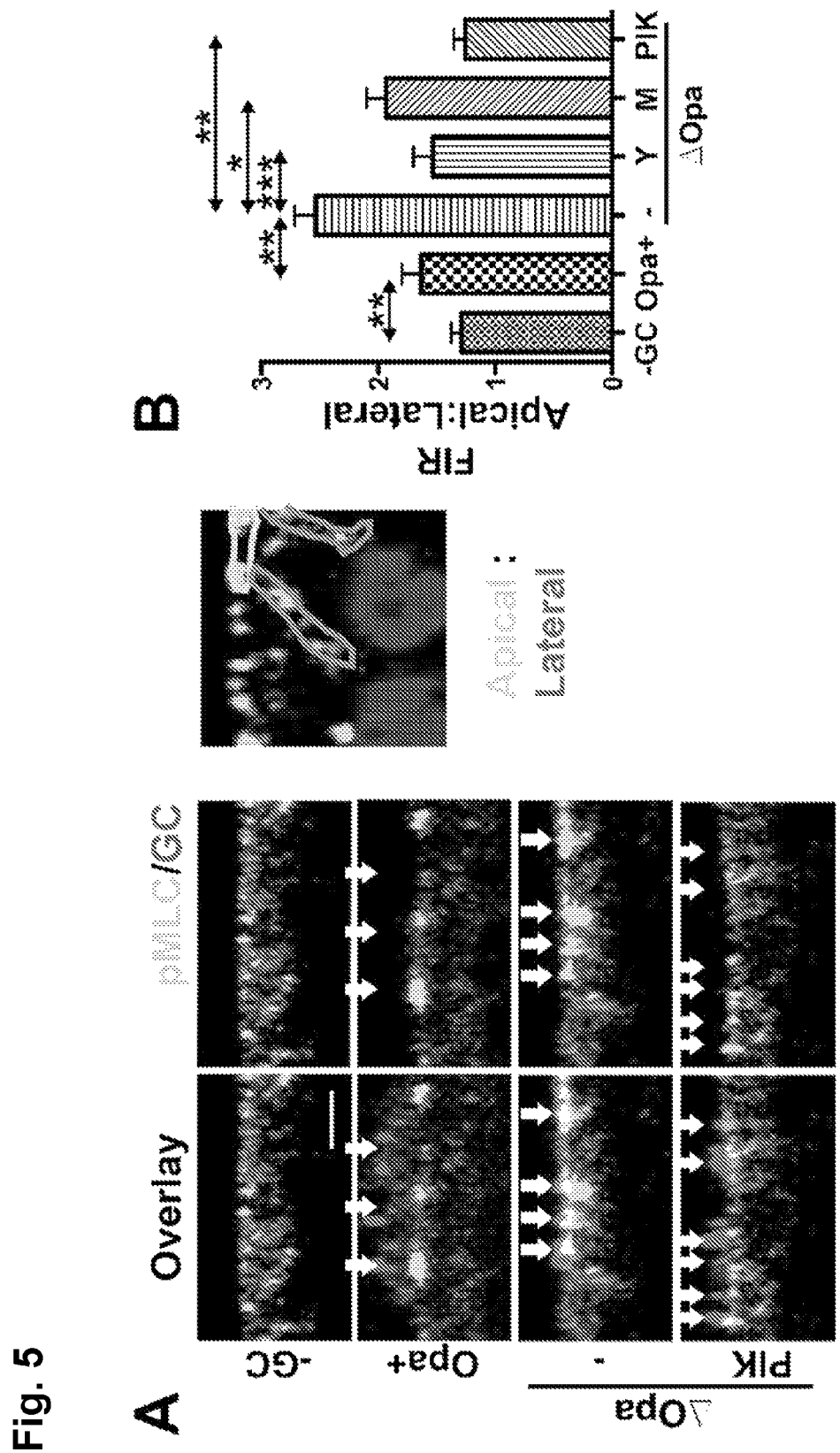
FIG. 5 shows Ng interaction increases the levels of phosphorylated MLC at the apical junction and apical membrane. (A-D) Polarized T84 cells were untreated or pre-treated with the ROCK inhibitor Y27632 (Y) and the MLCK inhibitor ML-7 (M) and PIK, and apically incubated with MS11Opa+ and ΔOpa for 6 h in the presence or absence of inhibitors. Cells were stained for phosphorylated MLC (pMLC) and Ng and analyzed using 3D-CFM. FIRs of pMLC at the apical to lateral region (A and B) and at the junctional to non-junctional region (C and D) were determined. Shown are representative xz (A) and xy images at the apical junctional location (C), FI maps (C, right panels), and the average FIR (±SD) (B and D) of >50 cells from three independent experiments. Arrows indicate Ng. Bar, 5 µm. (E-G) Polarized T84 cells were treated with inhibitors and incubated with Ng as above. Cells were then lysed and analyzed by Western blot probing for MLC, pMLC and β-tubulin. The blot was quantified by Phosphorimager. Shown are representative blots (E) and the average fold of increase (±SD) in pMLC:MLC (F) and MLC:tubulin (G) ratios over no Ng control from three independent experiments. *$p \leq 0.001$; $p \leq 0.01$; *$p \leq 0.05$.
Figure 5:
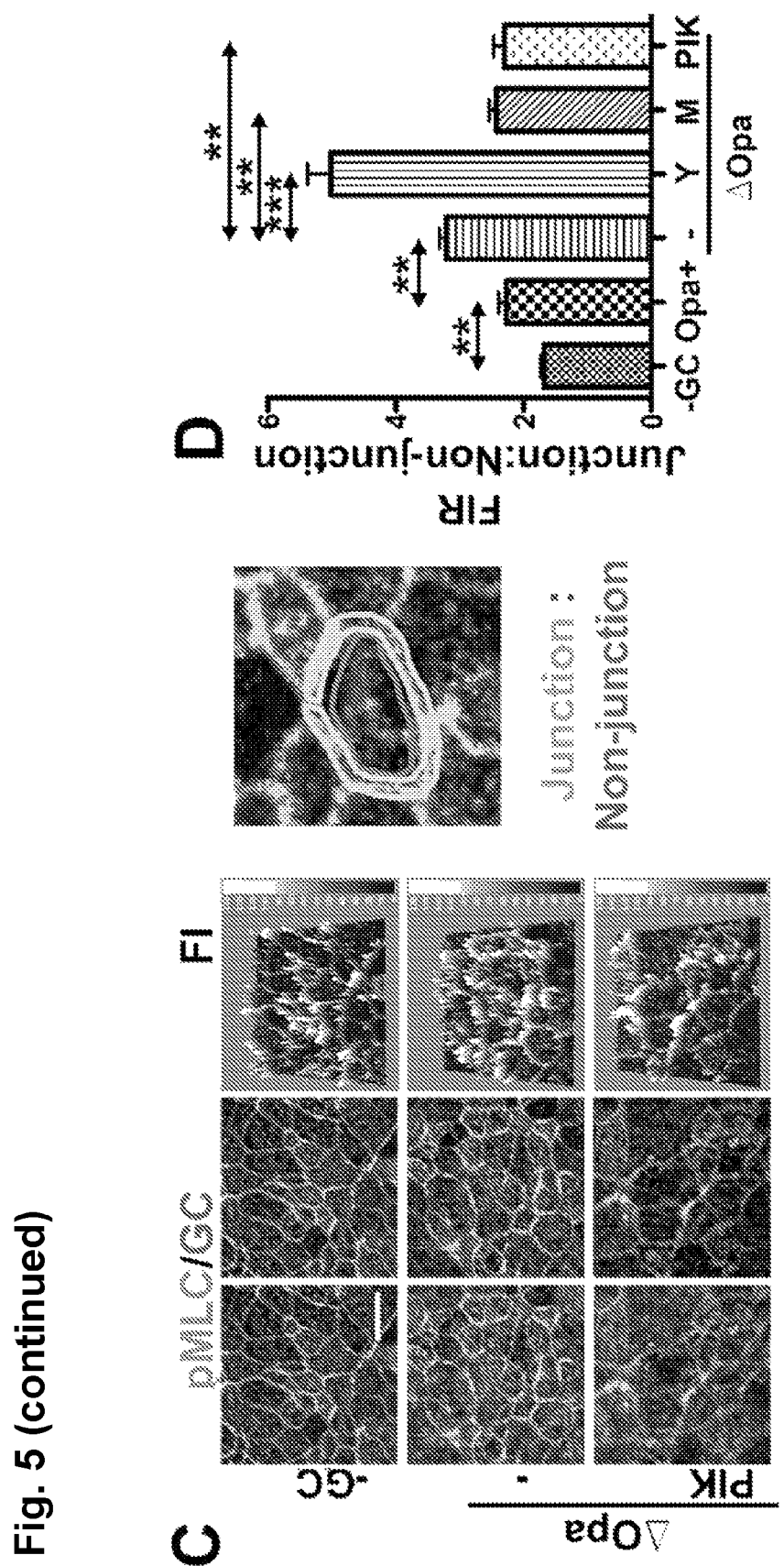
Figure 5:
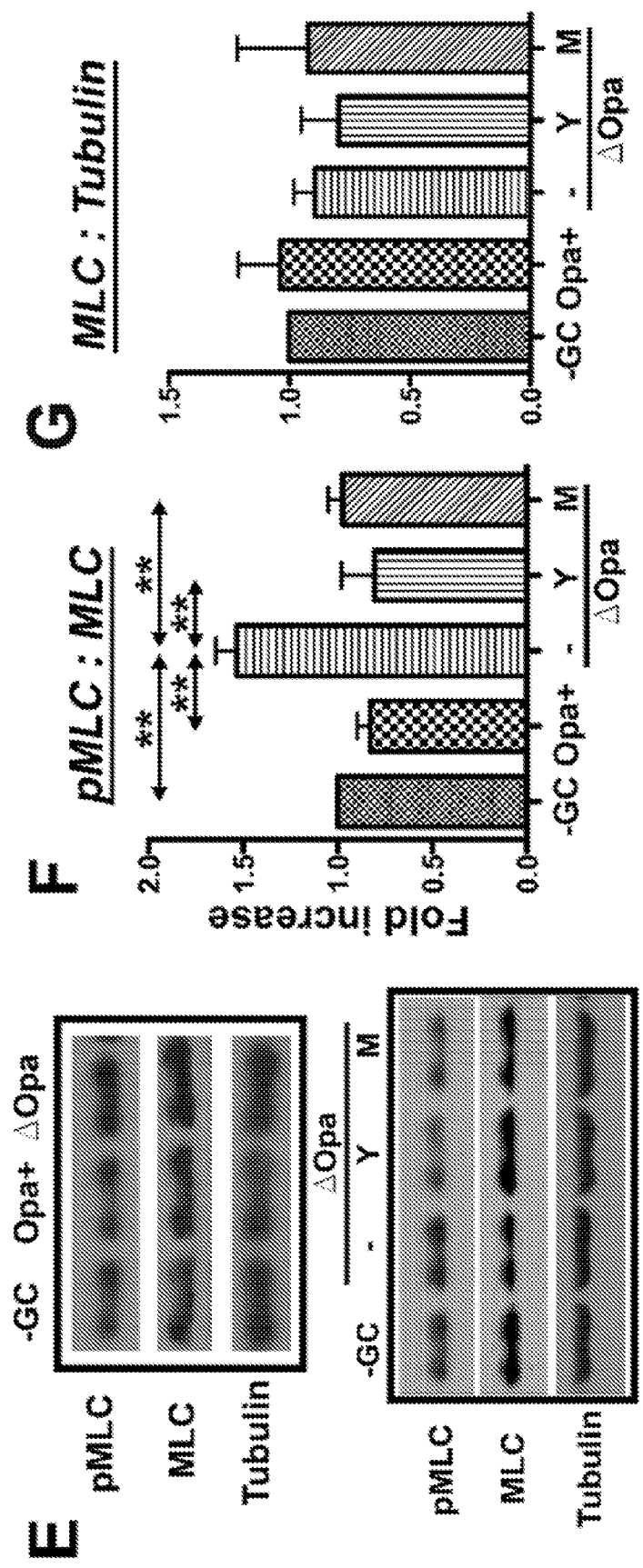
Figure 10:
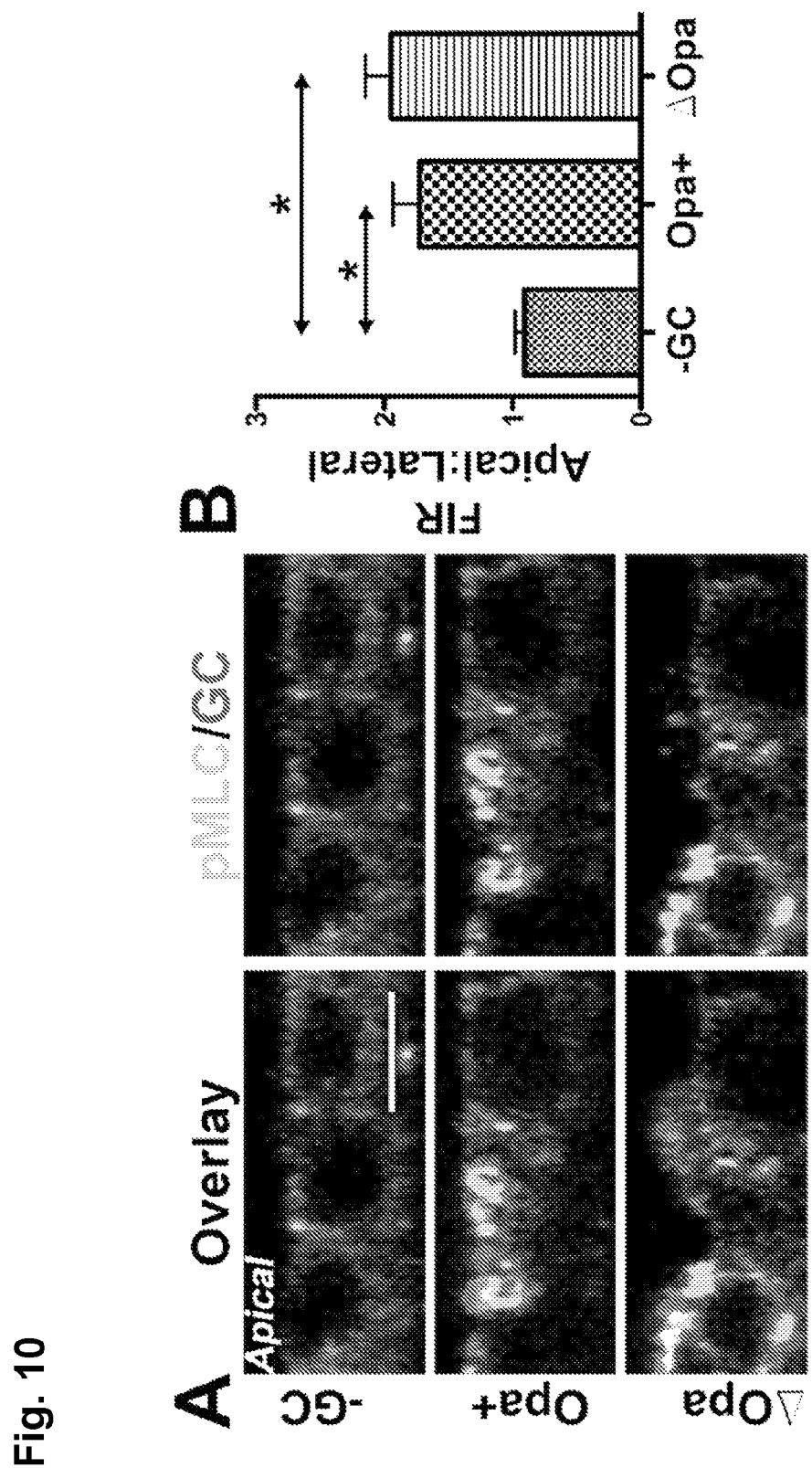
FIG. 10 shows Ng interaction increases the levels of phosphorylated MLC at the apical membrane of HEC-1-B cells. Polarized HEC-1-B cells were apically incubated with MS11Opa+ or ΔOpa at a MOI of 10 for 6 h. Cells were fixed, permeabilized, stained for phosphorylated MLC (pMLC) and Ng, and analyzed using 3D-CFM. The fluorescence intensity ratio (FIR) of pMLC at the apical to lateral region was determined. Shown are representative xz images (A) and the average FIR (±SD) (B) of >50 individual cells from more than three independent experiments. Arrows indicate Ng. Scale bar, 5 μm. *$p \leq 0.05$.

Ng induce and Opa suppresses the redistribution of active non-muscle myosin II in polarized and endocervical epithelial cells. Our finding of that Ng induce both epithelial exfoliation and apical junction disassembly in a NMII-dependent manner suggests that Ng regulate the activity of NMII in polarized epithelial cells. We examined the cellular distribution of active NMII after 6-h incubation with Ng, using antibody specific for phosphorylated myosin light chain (pMLC) and 3D-CFM. In uninfected polarized T84 (FIGS. 5A and 5C) and HEC-1-B cells (FIG. 10), pMLC was primarily localized at the apical junction. The polarized distribution of pMLC at the apical surface was quantified by the FIR of pMLC at the apical to the lateral (Apical:Lateral) membrane areas in individual cells using CFM images scanning across the apical and basolateral surfaces (FIGS. 5A and 5B). The polarized distribution pMLC at the apical junction was quantified by the FIR of pMLC at the junction to non-junction (Junction:Non-junction) areas of the apical region using CFM images scanning through the apical junction (FIGS. 5C and 5D). The apical inoculation of MS11Opa+ and MS11ΔOpa caused significant increases in apical:lateral FIR in both polarized T84 (FIGS. 5A and 5B) and HEC-1-B cells (FIG. 10), compared to the no Ng control. There were also significant increases in the junction:non-junction FIR in infected polarized T84 cells, compared to non-infected cells (FIGS. 5C and 5D). Moreover, both the apical:lateral and junction:non-junction FIRs were significantly higher in MS11ΔOpa-infected than those in MS11Opa+-infected T84 cells (FIGS. 5B and 5D), but this difference was not detected in HEC-1-B cells (FIG. 10). We further noticed that NMII at the apical surface appeared to accumulate at Ng adherent sites (FIG. 5A, middle panels, arrows).

To determine if Ng inoculation changes the activation level of NMII, we quantified the amount of pMLC and MLC by Western blot. Polarized T84 cells were incubated with or without MS11Opa+ or MS11ΔOpa apically for 6 h before lysis and Western blot analysis. The antibody staining density ratios of pMLC to MLC in MS11ΔOpa− but not MS11Opa+-inoculated cells were significantly higher than that in uninoculated epithelial cells (FIG. 5E, top panels, and 5F). However, Ng inoculation did not significantly change the staining density ratio of MLC to tubulin (FIG. 5G). Thus, MS11ΔOpa, but not MS11Opa+, increases the activation level of NMII.

Figure 6:
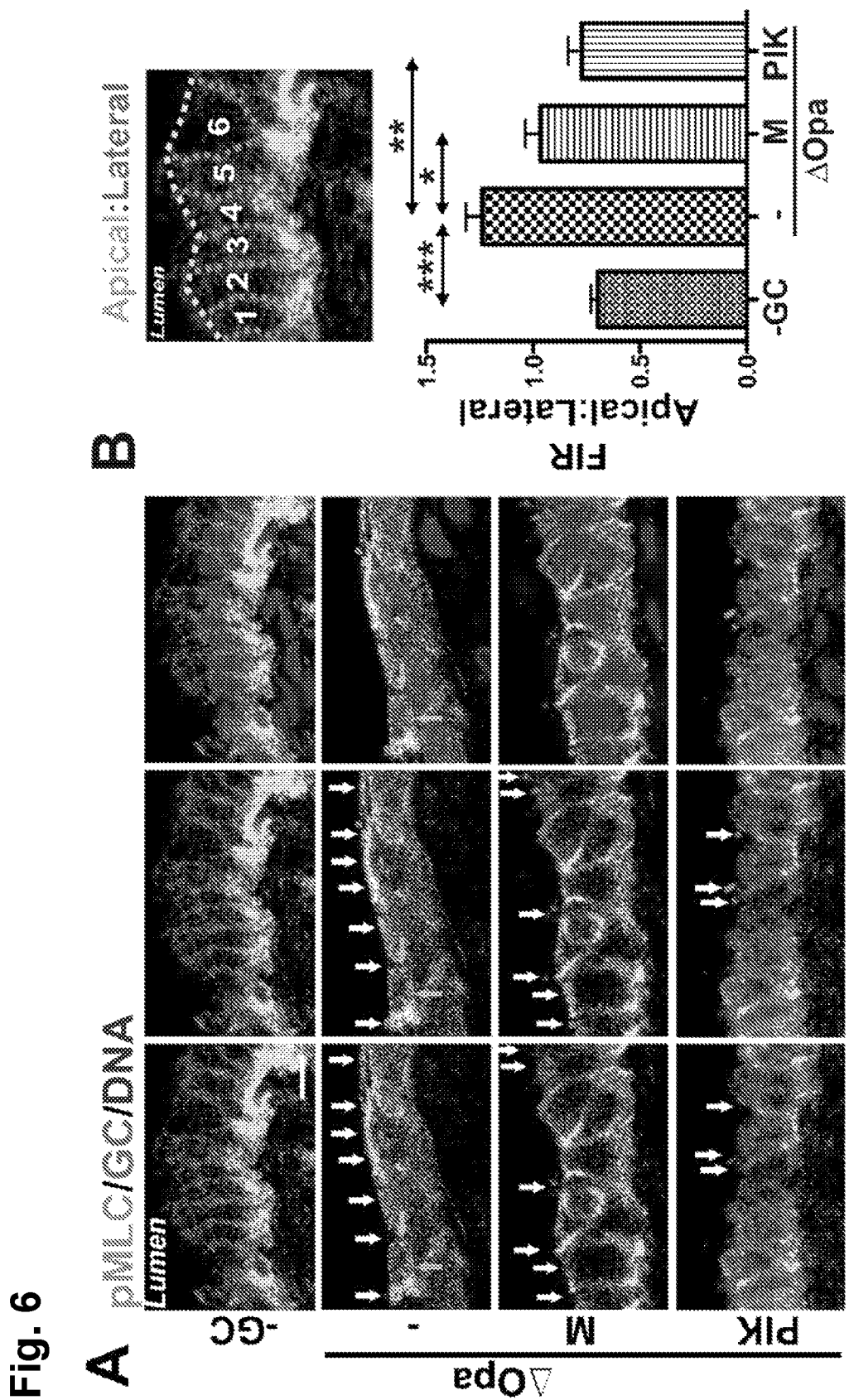
FIG. 6 shows the redistribution of active NMII in Ng infected endocervical epithelial cells of human tissue explants. Human endocervical tissue explants were untreated or pre-treated with the MLCK inhibitor ML-7 (M) or PIK and incubated with MS11ΔOpa in the presence or absence of the inhibitor for 24 h. Unassociated Ng were washed off at 6 and 12 h. The tissue was cryopreserved, sectioned, stained for Ng, pMLC, and DNA, and analyzed using 3D-CFM. Shown are representative images (A; white arrows, Ng; orange arrows, contacts between an exfoliating cell and its neighboring cells; Bar, 10 μm) and the average FIR (±SD) of pMLC at the apical to lateral region (B) from >40 epithelial cells of cervixes from two human subjects. *$p \leq 0.001$; $p \leq 0.01$; *$p \leq 0.05$.

To explore the possibility of that Ng induced NMII redistribution occurs in vivo, we incubated human endocervical tissue explants with MS11ΔOpa for 24 h. Cryosections of the endocervical tissue were stained for pMLC, Ng and nuclei. In addition to its apical junction localization, pMLC was concentrated at the basal surface of the endocervical epithelial cells contacting with the basal membrane (FIG. 6A, upper panels). When incubated with MS11ΔOpa, there was a redistribution of pMLC from the basal to apical surface, resulting in a significant higher apical:lateral FIR in Ng inoculated tissue explants than that in no Ng control (FIG. 6), similar to what we observed in polarized T84 (FIGS. 5A and 5B) and HEC-1-B cells (FIG. 10). Furthermore, pMLC at the apical surface of the endocervical epithelial cells also concentrated at Ng adherent sites (FIG. 6A, second row, white arrows), but not at the membrane of cells neighboring exfoliating cells (FIG. 6A, second row, orange arrows). These observations confirm that Ng increase the relative amount of activated NMII at the apical surface of the endocervical epithelial cells in human tissue explants. Our results from both human endocervical tissue explants and polarized epithelial cell lines indicate that Ng interactions cause an accumulation of activated NMII at Ng adherent sites and the apical membrane of columnar epithelial cells, and Opa expression suppresses both the activation and redistribution of NMII.

Differential roles of myosin light chain kinase and Rho-associated protein kinase in Ng induced NMII activation and redistribution. The activation of NMII is mediated by the phosphorylation of MLC by MLCK downstream of Ca$^{2+}$-activated calmodulin and/or by ROCK downstream of Rho GTPases. Our findings that Ng induced epithelial exfoliation and apical junctional disruption, as well as Ng transmigration, are inhibited by the MLCK and Ca$^{2+}$ but not ROCK inhibitors suggest that MLCK mediates the activation and redistribution of NMII triggered by Ng. We determined the effects of the MLCK and ROCK inhibitors on Ng induced MLC redistribution and phosphorylation using 3D-CFM and Western blot. Our 3D-CFM analysis found that treatment with the MLCK inhibitor ML-7 or PIK significantly reduced both the apical:lateral and junction:non-junction FIRs of pMLC in Ng infected epithelial cells (FIG. 5A-D), as well as the accumulation of pMLC at Ng adherent sites (FIG. 5A, bottom panels, arrows). However, treatment with the ROCK inhibitor Y27632 further increased the junction:non-junction FIR of pMLC in MS11ΔOpa-inoculated epithelial cells, while having similar inhibitory effects as the MLCK inhibitors on the apical:lateral FIR of pMLC (FIG. 5A-D). Our Western blot analysis showed that treatment with either the MLCK or the ROCK inhibitor reduced the pMLC:MLC but not the MLC:tubulin density ration in MS11ΔOpa-inoculated epithelial cells to basal levels (FIGS. 5F and 5G). Moreover, the MLCK inhibitors ML-7 and PIK significantly reduced the apical:lateral FIR of pMLC (FIG. 6) and pMLC accumulation at Ng adherent sites (FIG. 6A, white arrows) in MS11ΔOpa-inoculated endocervical tissue explants. These results suggest that both MLCK and ROCK are involved in the activation of MLC phosphorylation induced by MS11ΔOpa, but MLCK and ROCK distinctly regulate the subcellular location of active NMII with MLCK promoting and ROCK inhibiting the accumulation of active NMII to the apical junction.

Figure 7:
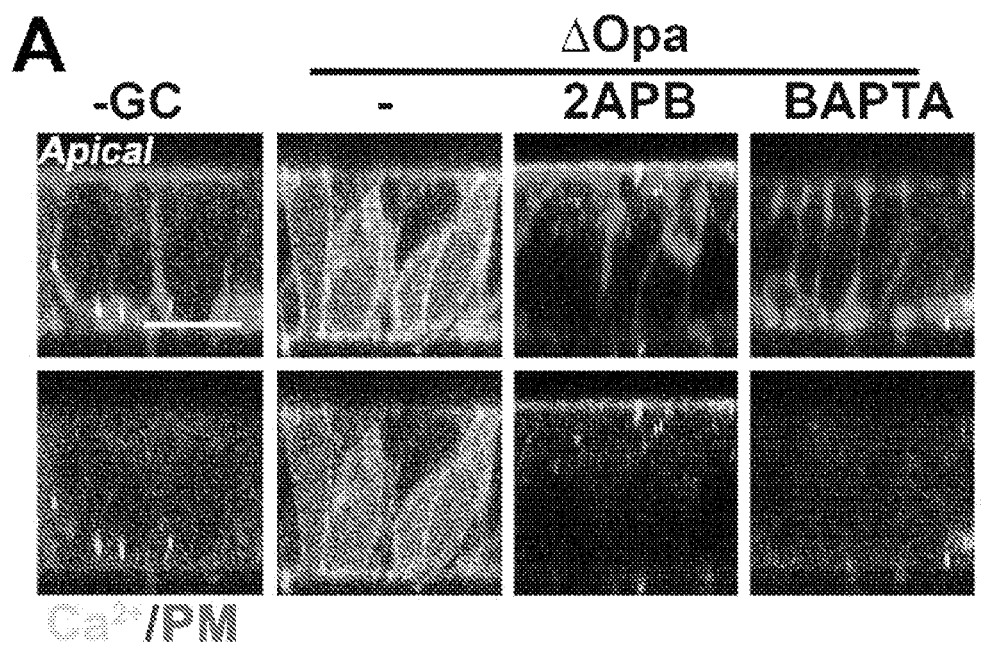
FIG. 7 shows Ng induced redistribution of active NMII depends on $Ca^{2+}$ flux. (A and B) Polarized T84 cells were incubated apically with or without MS11Opa+ or ΔOpa in the absence or presence of $Ca^{2+}$ inhibitors, 2APB (10 μM) or BAPTA (50 μM), for 4 h. Cells were incubated with the $Ca^{2+}$ indicator FluoForte and the membrane dye CellMask and analyzed using 3D-CFM. Shown are representative xz images (Bar, 5 μm) and the average MFI (±SD) of FluoForte in the cytoplasmic region of >50 cells from three independent experiments. (C-E) Polarized T84 cells were untreated or pre-treated with the Ca2+ inhibitors for 1 h and then apically incubated with MS11Opa+ or ΔOpa for 6 h in the presence or absence of inhibitors. Cells were stained for pMLC and Ng and analyzed by 3D-CFM. Shown are representative xy (C, left panels) and xz (C, right panels) images (Bar, 5 μm) and the average pMLC FIRs (±SD) of apical:lateral (D) and junction:non-junction (E) generated from >50 epithelial cells of three independent experiments. *$p \leq 0.001$; $p \leq 0.01$; *$p \leq 0.05$.
Figure 7:
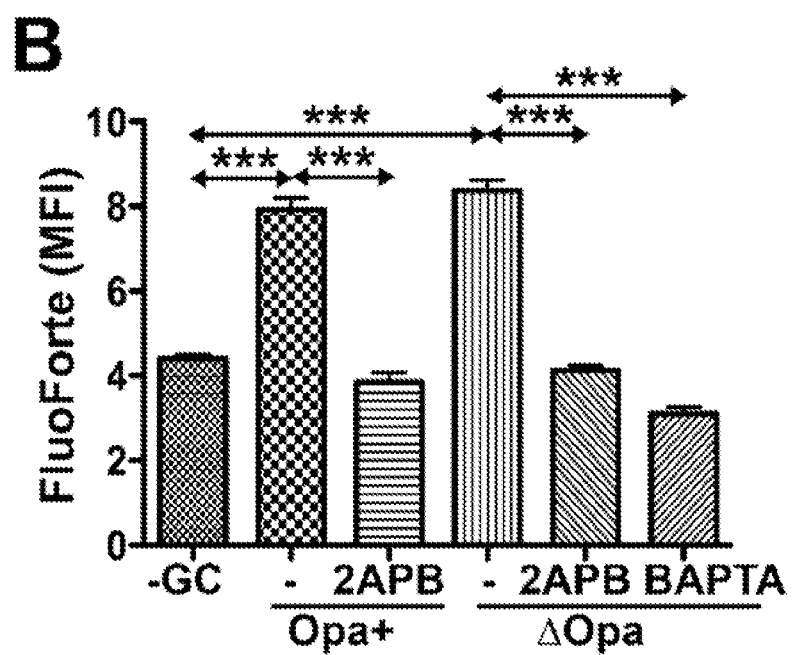
Figure 7:
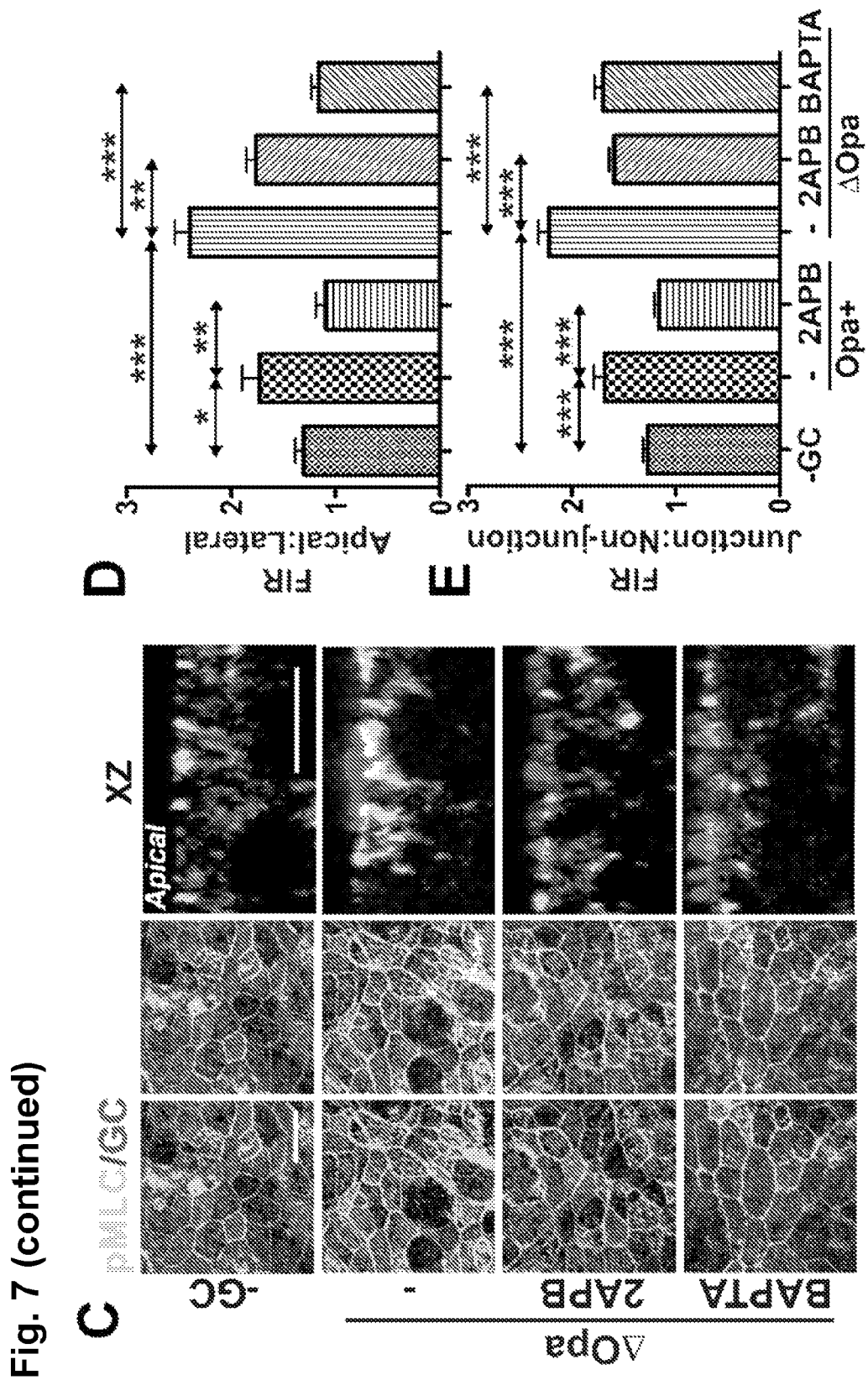
Figure 11:
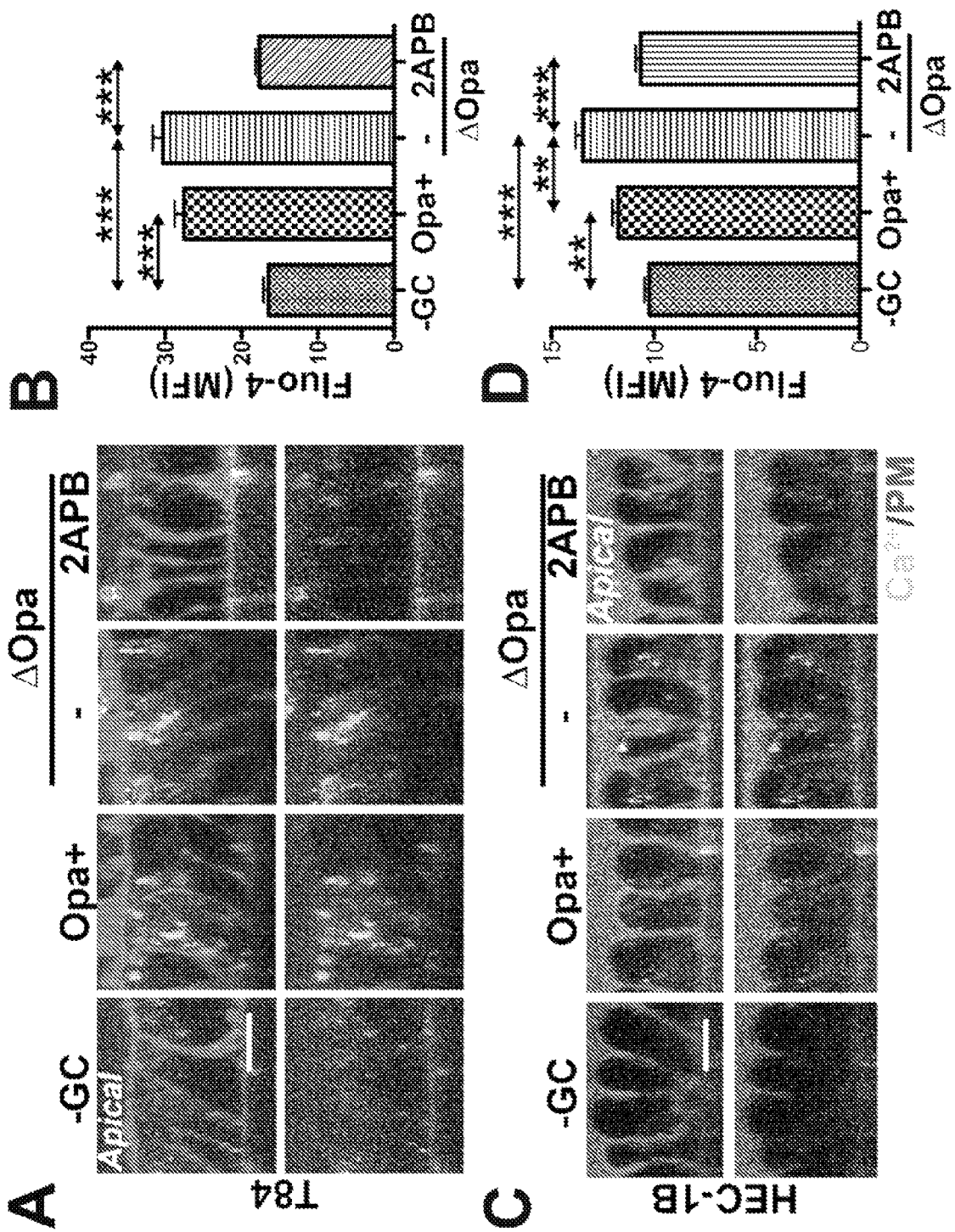
FIG. 11 shows Ng induce the elevation of the cytoplasmic $Ca^{2+}$ in polarized epithelial cells. Polarized T84 (A and B) and HEC-1-B cells (C and D) were incubated apically with or without MS11Opa+ or ΔOpa (MOI=10) in the absence or presence of the $Ca^{2+}$ inhibitor 2APB (10 μM) for 4 h. Then, cells were incubated with the $Ca^{2+}$ indicator Fluo-4 and the membrane dye CellMask and analyzed using 3D-CFM. Shown are representative xz images (Scale bar, 5 μm) (A and C) and the average mean fluorescence intensity (MFI) (±SD) of Fluo-4 in the cytoplasmic region (B and D) generated from >50 individual cells of three independent experiments. *$p \leq 0.001$; $p \leq 0.01$.

Ng inoculation induces $Ca^{2+}$-dependent redistribution of active NMII in polarized epithelial cells. A major upstream signaling molecule of MLCK is calmodulin that is activated by $Ca^{2+}$. To investigate if $Ca^{2+}$ is involved in Ng induced redistribution of active NMII, we determined if Ng inoculation would induce $Ca^{2+}$ flux in polarized epithelial cells. We used two $Ca^{2+}$ indicators, FluoForte (FIGS. 7A and 7B) and Fluo-4 (FIG. 11) to determine the cytoplasmic $Ca^{2+}$ level. Polarized T84 (FIGS. 7A and 7B, and FIG. 11A and FIG. 11B) and HEC-1-B (FIG. 11C and FIG. 11D) were incubated apically with MS11Opa+ or MS11ΔOpa for 4 h. The cells were then loaded with the fluorescent $Ca^{2+}$ indicator, and the cell membrane marked by the membrane dye CellMask. Cells were imaged using 3D-CFM (FIG. 7A, and FIGS. 11A and 11C). The mean fluorescence intensity (MFI) of the $Ca^{2+}$ dyes in individual cells was measured to estimate the cytoplasmic level of $Ca^{2+}$ (FIG. 7B, and FIGS. 11B and 11D). Compared to un-inoculated cells, polarized T84 cells and HEC-1-B inoculated with either MS11Opa+ or MS11ΔOpa exhibited significant increases in the MFI of both FluoForte (FIG. 7B) and Fluo-4 (FIGS. 11B and 11D). The MFIs of both the $Ca^{2+}$ indicators in MS11ΔOpa-inoculated epithelial cells were similar to those in MS11Opa+-inoculated cells (FIG. 7B and FIGS. 11B and 11D). Treatment with the inhibitor specific for $Ca^{2+}$ release from intracellular storages 2APB or the intracellular $Ca^{2+}$ chelator BAPTA brought the MFI of the $Ca^{2+}$ indicators in both MS11Opa+ and MS11ΔOpa-inoculated polarized epithelial cells back to the basal level as seen in uninoculated cells (FIG. 7B, and FIGS. 11B and 11D). These results suggest that Ng interacting with the apical surface of polarized epithelial cells increases the cytoplasmic level of $Ca^{2+}$ independently of Opa, by opening the intracellular $Ca^{2+}$ storages.

To determine whether Ng induced redistribution of active NMII depends on Ca2+, we treated polarized T84 cells with the $Ca^{2+}$ inhibitor 2APB or BAPTA before and during incubation with Ng. Both inhibitors decreased the apical:lateral (FIG. 7D) and the junction:non-junction FIRs (FIG. 7E) of pMLC in both MS11Opa+- and MS11ΔOpa-inoculated polarized epithelial cells, as well as the accumulation of pMLC at Ng adherent sites (FIG. 7C, right panels). The results in this and previous sections together suggest that $Ca^{2+}$-dependent activation of MLCK is responsible for Ng induced accumulation of active NMII at the apical junction and Ng adherent sites.

An important challenge in understanding of Ng pathogenesis in the FRT is to mechanistically explain why some Ng infections lead to invasive diseases while the rest of the infections remain localized. Prior to the present disclosure, a major research obstacle has been a lack of infection models that mimic the anatomic environment and process of Ng infection in vivo. This disclosure demonstrates use of a novel human endocervical tissue model with the support of the traditional polarized epithelial cells. The results demonstrate that Ng can penetrate into the subepithelium of the endocervix, while the efficiency of Ng penetration is regulated by Opa expression. Ng enter the subepithelium by disassembling the apical junction and inducing the exfoliation of polarized columnar epithelial cells. These events are caused by the elevation of the cytoplasmic $Ca^{2+}$ level and the activation and reorganization of NMII in epithelial cells. The expression of Opa inhibits Ng penetration by suppressing NMII activation and redistribution independently of $Ca^{2+}$ flux, thereby limiting Ng induced junction disruption and exfoliation of polarized endocervical epithelial cells.

Epithelial exfoliation serves as a protective mechanism of the host as the process sheds off host cell-associated pathogens. It has been reported that Ng induced exfoliation of squamous epithelial cells in the lower genital tract of the female mice reduces Ng colonization (Muenzner P, et al. Science. 2010; 329(5996):1197-201; Muenzner P, et al. CEACAM engagement by human pathogens enhances cell adhesion and counteracts bacteria-induced detachment of epithelial cells. J Cell Biol. 2005; 170(5):825-36). Bu in contrast, we show here that the exfoliation of columnar endocervical epithelial cells does not affect Ng adherence and invasion, rather it allows for an increase in Ng penetration into the subepithelium of the human endocervix. These conflicting results, observed in two different hosts and infection models, may be explained by differences between the types of epithelial cells and the mechanisms underlying Ng and apoptosis-induced exfoliation. A primary difference between multilayered squamous and monolayered columnar epithelial cells is the number of epithelial cell layers. Multilayered squamous epithelial cells can shed in layers with new layers growing underneath, while monolayered columnar epithelial cells exfoliate individual cells to protect the integrity of the epithelial barrier. Further, epithelial cells in our human endocervical tissue model shed as individuals but not as a layer. Based on these observations, it is plausible that individual cell shedding from the monolayered endocervical epithelium has a much less impact on Ng colonization than the shedding of epithelial layers from multilayered squamous cells.

A second difference between squamous and columnar epithelial cells is the cell-cell junction, the former by adherens junctions (E-cadherin-E-cadherin interactions) and focal adhesion (integrin-extracellular matrix interactions) and the latter by apical junctions (consisting of tight and adherens junctions) and desmosomes. Different junctional complexes suggest that Ng require two distinct mechanisms to regulate exfoliation and infection in the two types of epithelial cells. Here we show that Ng induce the exfoliation of the columnar endocervical epithelial cells by disrupting the apical junction through reorganizing its actomyosin support. While integrins may also be involved in the exfoliation of columnar epithelial cells as they mediate the interaction between epithelial cells and the basal membrane, the apical junction plays the essential role in holding and sealing the columnar epithelial monolayer. Ng induced apical junction disruption weakens the barrier function of the epithelium, thereby allowing the penetration of Ng into the endocervical subepithelium. In contrast, the exfoliation of squamous epithelial cells may not significantly impact the barrier function of the epithelium due to the presence of additional cell layers. These data together provide explanations for clinical observations that Ng rarely cause symptomatic vaginitis but can be found in the subepithelium of the endocervical biopsies from Ng infected women.

Whether Ng induced junctional disruption is sufficient to allow for Ng to penetrate through the paracellular space of the endocervical epithelium is not fully understood. But without intending to be constrained by any particular theory, the present disclosure is considered to confirm that Ng induced junctional disassembly also leads to a decrease in the polarity of endocervical epithelial cells in human tissues, supporting the existence of such an event in human infection.

The present disclosure provides a demonstration of a causative relationship between apical junction disruption and epithelial exfoliation, as the pharmacological inhibition of $Ca^{2+}$ flux and NMII activation and the natural expression of Opa suppress both Ng induced apical junction disassembly and exfoliation of polarized epithelial cells. This is in contrast to the exfoliation process involved in the columnar epithelial renewal and wound repair, where the apical junction remains intact. While the precise mechanism underlying the normal exfoliation of endocervical epithelial cells has not been examined, previous studies have shown that the barrier function of the epithelial monolayer is maintained by recruitment of apical junctional proteins and actomyosin to the plasma membrane of cells that neighbor the exfoliating cell. Actomyosin-generated forces in neighboring cells probably push exfoliating cells out while junctional proteins maintain the epithelial barrier. However, in Ng infected cells, the junctional proteins ZO1 and E-cadherin are redistributed from the apical junction to the cytoplasm and intracellular vesicles respectively, and NMII is recruited to Ng adherent sites and the apical junction, but not to the plasma membrane of cells neighboring exfoliating cells. As over-activation of NMII in perijunctional actomyosin rings can induce the disassembly and internalization of junctional proteins, data presented here indicate that the exfoliation of Ng infected endocervical epithelial cells is induced by Ng actively via the reorganization and activation of their NMII, modifying the normal exfoliation process to facilitate Ng penetration into the subepithelium.

The present disclosure also shows that NMII is a target of Ng to induce the disassembly of the apical junction and the exfoliation of the endocervical epithelial cells. When the activation and redistribution of NMII are inhibited by pharmacological reagents or Opa expression, Ng induced disassembly of the apical junction and exfoliation are reduced. While the important role of NMII in the apical junction prohibits us from use of a knockdown approach, the catalytic site-specific peptide inhibitor of MLCK PIK and the inhibitory effect of naturally expressed Opa have confirmed the results. The analysis is this disclosure further suggests that Ng induced NMII activation that leads to exfoliation and Ng transmigration primarily depends on MLCK- rather than ROCK-mediated phosphorylation of MLC. Even though both MLCK and ROCK contribute to the phosphorylation of MLC, the two differentially regulate the distribution of active NMII, as the ROCK inhibitor further increases while the MLCK inhibitors reduce the level of active NMII in the apical junction. This result suggests that the subcellular location rather than the level of NMII activation is important for Ng infection.

Using MS11ΔOpa, we found that Opa modulates Ng penetration into the endocervical epithelium and Ng induced columnar epithelial exfoliation by regulating the activation and redistribution of NMII, a target of Opa different from those in squamous epithelial cells. These data suggest the same Opa may use different mechanisms to suppress the exfoliation of polarized endocervical and non-polarized ectocervical epithelial cells. The exact mechanism by which Opa inhibits NMII activity is unknown. The inhibitory effects of Opa may be mediated through engaging CEACAMs, as CEACAMs are the primary host receptors for Opa and function to enhance cell-cell adherence and suppress cell signaling. This disclosure shows that MS11ΔOpa induced a significantly higher level of pMLC accumulation in the apical junction in CEACAM-expressing T84 cells than MS11Opa+ (FIG. 5D), but increased the pMLC accumulation to a level similar to MS11Opa+ in HEC-1-B cells that do not express CEACAMs (FIG. 11). These results support the notion that CEACAMs are involved in suppressing Ng induced NMII redistribution. While potentially involved in the exfoliation of both squamous and columnar epithelial cells, CEACAMs may differentially modulate signaling induced by Ng, due to distinct distribution of CEACAMs and organizations of signaling, cytoskeleton, and cell-cell junctions in the two types of epithelial cells. Results of this disclosure also show that Ng induced NMII activation depends on $Ca^{2+}$ flux that can activate MLCK via calmodulin. However, MS11Opa+ and MS11ΔOpa elevate the cytoplasmic $Ca^{2+}$ to similar levels. This result suggests that Opa inhibits Ng induced NMII activation in a $Ca^{2+}$-independent manner, such as by activating MLC phosphatase that dephosphorylates MLC or through modulating Ng epithelial physical interactions. By interacting with CEACAMs on epithelial cells and LOS on neighboring Ng, Opa potentially alters the physical tensions that Ng exert onto the mucosal surface, consequently changing the organization of NMII beneath the plasma membrane of epithelial cells. Since different isoforms of the 11 Opa proteins have different binding abilities to CEACAMs, they can modulate Ng epithelial interactions and signaling distinctly when Opa undergoes phase variation.

This disclosure is believed to be the first to utilize human endocervical tissue explants to examine the mechanism by which Ng establish infection in this in vivo location. The results indicate that Ng manipulate the epithelial barrier by regulating host cell signaling and cytoskeletal systems for their infection. The nature and level of Ng mediated manipulation are modulated by phase variation of Ng surface molecules and types of epithelial cells that Ng interact with, which enable Ng to infect various regions of the FRT and generate different infection outcomes. The disclosure thus includes human endocervical tissue explants as described herein, as well as methods of using such explants to analyze test agents for their effect on endocervical tissues, and/or for evaluating the effects of test agents on infectious agents.

Materials and methods Neisseria strains and epithelial cells. *N. gonorrhoeae* strain MS11 that expressed both pili and Opa (MS11Pil+Opa+) was obtained from Dr. Herman Schneider, Walter Reed Army Institute for Research. A derivative of this strain, MS11ΔOpa, has previously been described. Ng were grown on plates with Ng media (Difco, BD Bioscience, Franklin Lakes, N.J.) and 1% Kellogg's supplement for 16-18 h before inoculation. Pil+Opa+ colonies were identified based on their morphology using a dissecting light microscope. The concentration of Ng in suspension was determined using a spectrophotometer and inoculated at MOI 10:1. Human colorectal carcinoma cell line, T84 (ATCC, Manassas, Va.), was maintained in DMEM:Ham F12 (1:1) supplemented with 7% heat-inactivated fetal bovine serum (FBS). Human endometrial adenocarcinoma cell line, HEC-1-B (ATCC), was maintained in Eagles MEM alpha medium supplemented with 10% heat-inactivated FBS. Cells were seeded at 6×104 per transwell (6.5 mm diameter and 3 μm pore size, Corning, Corning, N.Y.) and cultured for ~10 days until transepithelial electrical resistance (TEER) reached >1000Ω (T84) or >300Ω (HEC-1-B). TEER was measured using a Millicell ERS volt-ohm meter (EMD Millipore, Billerica, Mass.).

Human endocervical tissue explants. The tissue explants were cultured as previously described. Endocervical tissues were obtained from patients undergoing voluntary hysterectomies and received within 24 h post-surgery. Samples were cut into ~2.5 cm (L)×0.6 cm (W)×0.3 cm (H) pieces, incubated in CMRL-1066 (GIBCO, Gaithersburg, Md.) plus antibiotics for 24 h, and then switched to antibiotic-free media for 24 h.

Immunofluorescence analysis of human endocervical tissue explants. Individual endocervical tissue pieces were incubated with Ng at a MOI of ~10 (based on the average number of endocervical epithelial cells in endocervical tissue pieces) in the presence or absence of the MLCK inhibitor ML-7 (10 μM, EMD Millipore) and PIK (100 μM) (54) on transwells for 24 h. Unassociated Ng were removed by extensive washes at 6 and 12 h. The tissue was fixed, embedded in gelatin, cryopreserved, sectioned crossing the apical and basolateral surfaces of the epithelium, stained for ZO1 (BD Bioscience), pMLC (Cell Signaling Technology, Beverly, Mass.), and Ng (51) by specific antibodies, and nuclei by DAPI (Life Technologies, Carlsbad, Calif.), and analyzed using CFM (Zeiss LSM 710, Carl Zeiss Microscopy LLC, Oberkochen, Germany). Images were acquired as Z-series of 0.37 μm slices, and 3D composites obtained using the NIH ImageJ software.

To quantify epithelial exfoliation, the number of Ng associated cells localized on the top of the epithelial monolayer (exfoliated) and the total number of Ng associated epithelial cells was counted by visual inspection in each randomly acquired image, to determine the percentage of exfoliated cells. To estimate the level of Ng penetration into the subepithelium, the number of non-exfoliated epithelial cells (in clearly visible epithelial monolayers) with basal Ng staining and the total number of Ng associated epithelial cells were visually counted to calculate the percentage of infected epithelial cells with Ng penetration into the basolateral side. To evaluate the disruption of the apical junction, the number of Ng associated epithelial cells that lost continuously apical staining of the junctional protein ZO1 and the total number of Ng associated epithelial cells were visually counted to calculate the percentage of Ng associated epithelial cells with apical junction disassembly. To quantify the redistribution of pMLC, the fluorescence intensity ratios (FIR) of pMLC staining at the apical to lateral in individual epithelial cells were determined using average FI as previously described.

Immunofluorescence analysis of polarized epithelial cells. Cells were pretreated with or without NMII kinase inhibitors, Y27632 (10 μM, EMD Millipore), ML-7 (10 μM, EMD Millipore) and PIK (100 μM) or Ca2+ inhibitors, 2APB (10 μM, EMD Millipore) and BAPTA (50 μM, EMD Millipore) for 1 h, and incubated with Ng in the presence or absence of the inhibitors for 6 h. Cell were washed and fixed with 4% paraformaldehyde, permeabilized with 1% Triton X100, and stained with anti-E-cadherin (BD Bioscience), anti-pMLC (Cell Signaling Technology, Carlsbad, Calif.), anti-Ng antibodies, and DAPI for nuclei. Cells were analyzed by CFM. Images were acquired as Z-series of 0.37 μm slices, and 3D composites obtained. Epithelial exfoliation will be quantified using xz images as described for the tissue explants. The distribution of E-cadherin and pMLC was quantitatively analyzed by measuring the FIR at the apical junctional to the cytoplasmic area (from xy images) or at the apical to lateral surface area (from xz images) in individual cells.

Fence functional of the apical junction. Polarized T84 cells were incubated with Ng apically for 6 h. Then the cells were incubated with the CellMask dye (5 μg/ml, Life Technologies) in the basolateral chamber only for 15 min, and xz images were acquired using Leica TCS SP5X confocal microscope (Leica Microsystems, Buffalo Grove, Ill.). The number of epithelial cells displaying CellMask staining at the apical membrane was countered visually as the percentage of the total number of epithelial cells in each randomly acquired image.

Immunoblotting analyses. Polarized T84 cells, apically incubated with Ng for 6 h with or without inhibitors, were lysed by RIPA buffer [1% NP-40, 0.5% deoxycholate, 0.1% SDS, 50 mM Tris-HCl pH 7.4, 150 mM NaCl, 1 mM EGTA, 2 mM EDTA, 1 mM $Na_3VO_4$, 50 mM NaF, 10 mM $Na_2PO_4$, and proteinase inhibitor cocktail (Sigma-Aldrich, St. Louis, Mo.)]. Lysates were resolved using SDS-PAGE gels (Bio-Rad, Hercules, Calif.) and analyzed by Western blot. Blots were stained for pMLC or MLC (Cell Signaling Technology), stripped, and reprobed with anti-β-tubulin antibody (Santa Cruz, Santa Cruz, Calif.). Blots were quantified using a Fujifilm LAS-3000 (Fujifilm Medical Systems U.S.A., Inc., Stamford, Conn.).

Ng adherence, invasion, and transmigration assays. The assays were performed as previously described. Briefly, polarized epithelial cells that were pretreated with or without the inhibitors for 1 h were incubated apically with Ng at 37° C. for 3 h for adherence and 6 h for invasion and transmigration assays with or without the inhibitors. Ng in the basolateral media were cultured and counted as transmigrated bacteria. Cells were washed and lysed to count adherent Ng. Cells were treated with gentamicin, washed, and lysed to count bacteria that were resistant to gentamicin treatment as invaded Ng.

Calcium imaging. T84 cells were seeded at 1×105 per transwell on the underside of transwells and cultured for ~10 days until TEER reached >1000Ω. Cells were pre-treated with or without the $Ca^{2+}$ inhibitors, 2APB (10 μM, Sigma, Saint Louis, Mo.) and BAPTA (50 μM, Sigma), for 1 h and incubated with Ng (MOI of 10) apically in the presence or absence of the inhibitors for 4 h. Then cells were incubated with the fluorescent $Ca^{2+}$ indicator Fluoforte (100 μg/ml, Enzo Life Sciences, Farmingdale, N.Y.) or Fluo-4 (100 μM, Life Technologies) for 1 h. Confocal xz images were acquired in the presence of the membrane dye CellMask (5 mg/ml, Life Technology) using Leica TCS SP5X confocal microscope (Leica Microsystems, Buffalo Grove, Ill.), based on the instruction by manufacturers. To quantify the intracellular $Ca^{2+}$ level, the cytoplasmic region of individual cells was manually selected based on the CellMask staining in randomly acquired confocal images, and the mean fluorescent intensity (MFI) of Fluoforte and Fluo-4 in the cytoplasmic region was measured using the NIH ImageJ software.

Statistical analysis. Statistical significance was assessed using the Student's t-test by Prism software (GraphPad Software, La Jolla, Calif.).

EXAMPLE 2

This Example provides data demonstrating compositions comprising PIK as discussed above for use in intravaginal prophylaxis and/or therapy of Ng. In particular this Example demonstrates that PIK can prohibit Ng from damaging the epithelial barrier and penetrating into human cervical tissues, which are important steps for Ng to establish penetrating infection (FIG. 12). In addition, PIK suppresses Ng growth (FIG. 13). Effectiveness of PIK in preventing Ng infection is supported using both 3D human epithelial cell and cervical tissue explant models (FIG. 12). Therefore, it is expected that PIK will function as an effective agent for use as an intravaginally applied Ng preventative because the in vitro and ex vivo models of human epithelial cells and cervical tissue explants described herein show robust inhibition of PIK against Ng penetration into the human cervical epithelium (FIG. 12) and Ng growth (FIG. 13). A gel-based formula of PIK and a test of its efficacy in preventing Ng penetration using the human cervical tissue model as shown in FIG. 12.

While the invention has been described through specific embodiments, routine modifications will be apparent to those skilled in the art and such modifications are intended to be within the scope of the present invention.

---

---

What is claimed is:

1. A method for prophylaxis and/or therapy of a reproductive tract infection by *Neisseria gonorrhoeae*, the method comprising intravaginal administration of a composition comprising an effective amount of PIK, or ML-7, or a combination thereof.

2. The method of claim 1 wherein the composition further comprises a mucoadhesive agent.

3. The method of claim 1, wherein the composition comprises a pharmaceutically acceptable excipient.

4. The method of claim 1, wherein the composition comprises a gel.

5. The method of claim 1, wherein the composition comprises a polymer.

6. The method of claim 5, wherein the polymer is a biodegradable polymer.

7. The method claim 1 wherein the intravaginal administration comprises vaginal insertion of a device comprising the composition.

8. The method of claim 1, wherein the composition comprises the PIK, wherein the PIK comprises SEQ ID NO:1, wherein at least one amino acid of SEQ ID NO:1 is in D-form.

9. The method of claim 1, wherein administering the composition comprising an effective amount of PIK, or ML-7, or the combination thereof, decreases epithelial exfoliation of endocervical tissue that is in contact with *Neisseria gonorrhoeae*.

10. The method of claim 9, comprising administering an effective amount of the ML-7.

11. The method of claim 8, wherein at least one of the following occurs:
  i) penetration of *Neisseria gonorrhoeae* into endocervical epithelia of the individual is inhibited;
  ii) transmigration of *Neisseria gonorrhoeae* across polarized endocervical epithelial cells is inhibited;
  iii) growth of *Neisseria gonorrhoeae* in the individual is inhibited.

\* \* \* \* \*